US012588675B2

(12) United States Patent
Jovanovic et al.

(10) Patent No.: US 12,588,675 B2
(45) Date of Patent: *Mar. 31, 2026

(54) SYNERGISTIC ANTIBACTERIAL ACTIVITY OF MEDIUM POLARITY OILS IN COMBINATION WITH ANTIBACTERIAL AGENTS ON BACTERIAL BIOFILMS

(71) Applicant: SMITH & NEPHEW, INC., Memphis, TN (US)

(72) Inventors: Aleksa Jovanovic, Fort Worth, TX (US); Lei Shi, Mansfield, TX (US); Eric Roche, Fort Worth, TX (US); Paul Renick, Fort Worth, TX (US)

(73) Assignee: SMITH & NEPHEW, INC., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/130,042

(22) Filed: Apr. 3, 2023

(65) Prior Publication Data

US 2023/0345938 A1 Nov. 2, 2023

Related U.S. Application Data

(63) Continuation of application No. 17/545,409, filed on Dec. 8, 2021, now Pat. No. 11,641,856, which is a (Continued)

(51) Int. Cl.

| | |
|---|---|
| *A01N 59/12* | (2006.01) |
| *A01N 25/04* | (2006.01) |
| *A01N 25/30* | (2006.01) |
| *A01N 37/02* | (2006.01) |
| *A01N 37/46* | (2006.01) |
| *A01N 59/16* | (2006.01) |
| *A61K 9/00* | (2006.01) |
| *A61K 9/06* | (2006.01) |
| *A61K 31/23* | (2006.01) |
| *A61K 31/25* | (2006.01) |
| *A61K 31/625* | (2006.01) |
| *A61K 31/7036* | (2006.01) |
| *A61K 31/79* | (2006.01) |
| *A61K 33/18* | (2006.01) |
| *A61K 33/38* | (2006.01) |
| *A61K 38/12* | (2006.01) |
| *A61K 45/06* | (2006.01) |
| *A61K 47/10* | (2017.01) |

(Continued)

(52) U.S. Cl.
CPC ............. *A01N 37/02* (2013.01); *A01N 25/04* (2013.01); *A01N 25/30* (2013.01); *A01N 37/46* (2013.01); *A01N 59/12* (2013.01); *A01N 59/16* (2013.01); *A61K 9/0014* (2013.01); *A61K 9/06* (2013.01); *A61K 31/23* (2013.01); *A61K 31/25* (2013.01); *A61K 31/625* (2013.01); *A61K 31/7036* (2013.01);

*A61K 31/79* (2013.01); *A61K 33/18* (2013.01); *A61K 33/38* (2013.01); *A61K 38/12* (2013.01); *A61K 45/06* (2013.01); *A61K 47/10* (2013.01); *A61K 47/14* (2013.01); *A61K 47/26* (2013.01); *A61K 47/38* (2013.01); *A61L 26/0066* (2013.01); *A61L 27/025* (2013.01); *A61L 27/047* (2013.01); *A61L 27/306* (2013.01); *A61L 27/34* (2013.01); *A61L 27/52* (2013.01); *A61L 27/54* (2013.01); *A61L 29/02* (2013.01); *A61L 29/085* (2013.01); *A61L 29/106* (2013.01); *A61L 29/145* (2013.01); *A61L 29/16* (2013.01); *A61L 31/022* (2013.01); *A61L 31/028* (2013.01); *A61L 31/088* (2013.01); *A61L 31/10* (2013.01); *A61L 31/145* (2013.01); *A61L 31/16* (2013.01); *A61P 31/04* (2018.01); *A61L 2300/404* (2013.01); *A61L 2300/406* (2013.01); *A61L 2420/04* (2013.01)

(58) Field of Classification Search
None
See application file for complete search history.

(56) References Cited

U.S. PATENT DOCUMENTS

| | | | |
|---|---|---|---|
| 5,217,493 A | 6/1993 | Raad et al. | |
| 6,399,092 B1 | 6/2002 | Hobson et al. | |

(Continued)

FOREIGN PATENT DOCUMENTS

| | | | |
|---|---|---|---|
| CA | 2656332 A1 * | 1/2008 | ............. A61K 33/00 |
| CN | 1045701 | 10/1990 | |

(Continued)

OTHER PUBLICATIONS

Goldenheim, In vitro efficacy of povidone-iodine solution and cream against methicillin-resistant *Staphylococcus aureus*, Postgrad Med Journal, 1993:69 Suppl 3:S62-5 (Year: 1993).*

(Continued)

*Primary Examiner* — Jennifer A Berrios
(74) *Attorney, Agent, or Firm* — Norton Rose Fulbright US LLP

(57) ABSTRACT

The compositions of the present invention comprise at least one medium polarity oil and at least one antibacterial agent, the combination of which produces a synergistic antibacterial effect against bacterial biofilms. Methods are disclosed for the reduction of bacteria in and/or elimination of bacterial biofilms on biological and non-biological surfaces, as well as methods for the treatment of wounds, skin lesions, mucous membrane lesions, and other biological surfaces infected or contaminated with bacterial biofilms.

11 Claims, 8 Drawing Sheets

Related U.S. Application Data continuation of application No. 16/529,303, filed on Aug. 1, 2019, now Pat. No. 11,197,476, which is a continuation of application No. 15/754,703, filed as application No. PCT/US2016/048110 on Aug. 23, 2016, now abandoned.

(60) Provisional application No. 62/209,181, filed on Aug. 24, 2015.

(51) Int. Cl.

| | | |
|---|---|---|
| A61K 47/14 | (2017.01) | |
| A61K 47/26 | (2006.01) | |
| A61K 47/38 | (2006.01) | |
| A61L 26/00 | (2006.01) | |
| A61L 27/02 | (2006.01) | |
| A61L 27/04 | (2006.01) | |
| A61L 27/30 | (2006.01) | |
| A61L 27/34 | (2006.01) | |
| A61L 27/52 | (2006.01) | |
| A61L 27/54 | (2006.01) | |
| A61L 29/00 | (2006.01) | |
| A61L 29/08 | (2006.01) | |
| A61L 29/10 | (2006.01) | |
| A61L 29/14 | (2006.01) | |
| A61L 29/16 | (2006.01) | |
| A61L 31/02 | (2006.01) | |
| A61L 31/08 | (2006.01) | |
| A61L 31/10 | (2006.01) | |
| A61L 31/14 | (2006.01) | |
| A61L 31/16 | (2006.01) | |
| A61P 31/04 | (2006.01) | |

(56) References Cited

U.S. PATENT DOCUMENTS

| | | | |
|---|---|---|---|
| 2009/0155215 A1 | 6/2009 | Collins et al. | |
| 2009/0263439 A1 | 10/2009 | Casas-Sanchez et al. | |
| 2009/0312279 A1 | 12/2009 | Mookerjee et al. | |
| 2010/0203139 A1 | 8/2010 | Baker et al. | |
| 2012/0201902 A1 | 8/2012 | Modak et al. | |
| 2013/0085103 A1 | 4/2013 | Mohan et al. | |
| 2016/0015047 A1 | 1/2016 | Gawande et al. | |

FOREIGN PATENT DOCUMENTS

| | | | | |
|---|---|---|---|---|
| CN | 1209065 | 2/1999 | | |
| CN | 1292641 | 4/2001 | | |
| CN | 1294519 | 5/2001 | | |
| CN | 1327382 | 12/2001 | | |
| CN | 1572301 | 2/2005 | | |
| CN | 1600300 | 3/2005 | | |
| CN | 1744905 | 3/2006 | | |
| CN | 101919807 | 12/2010 | | |
| CN | 102210648 | 10/2011 | | |
| CN | 102223876 | 10/2011 | | |
| CN | 102939097 | 2/2013 | | |
| CN | 103720640 | 4/2014 | | |
| CN | 104302359 | 1/2015 | | |
| CN | 104586888 | 5/2015 | | |
| CN | 104644667 | 5/2015 | | |
| JP | 2012056854 | 3/2012 | | |
| JP | 2013245187 | 12/2013 | | |
| WO | WO 2004/052308 | 6/2004 | | |
| WO | WO 2011/002929 | 1/2011 | | |
| WO | WO 2011/035158 | 3/2011 | | |
| WO | WO-2011089379 A2 * | 7/2011 | ............ | A01N 59/16 |
| WO | WO 2014/201541 | 12/2014 | | |

OTHER PUBLICATIONS

Thorn et al., In vitro comparison of antimicrobial activity of iodine and silver dressings against biofilms, Journal of Wound Care vol. 18 , No. 8 , Aug. 2009 (Year: 2009).*

A Versatile In Vitro Biofilm Model Using Two Wound Pathogens to Screen Formulations, 2010 Wound Healing Society Annual Meeting, Poster Abstract BRC09, Apr. 18, 2010, Orlando, FL.

"Research on Microbial Biofilms," National Institutes of Health, PA No. PA-03-047, Dec. 20, 2002. Accessed on Aug. 25, 2018 on internet at https://grants.nih.gov/grants/pa-files/pa-03-047.html.

Akiyama et al., "Assessment of Cadexomer Iodine against *Staphylococcus aureus* Biofilm In vivo and In vitro Using Confocal Laser Scanning Microscopy" *J Dermatol* 2004, 31(7), 529-34.

Attinger et al., "Clinically Addressing Biofilm in Chronic Wounds" *Advances in Wound Care* 2012, 1(3), pp. 127-132.

Bjarnsholt, "Why Chronic Wounds Will Not Heal: A Novel Hypothesis," Wound Repair and Regeneration, 2008.

Borriello, et al., "Oxygen Limitation Contributes to Antibiotic Tolerance of Pseudomonas Aeruginosa in Biofilms," Antimicrobial Agents and Chemotherapy, 48(7); 2659-2664, 2004.

Hess et al., "Antibacterial Synergy of Glycerol Monolaurate and Aminoglycosides in Staphylococcus aureus Biofilms" *Antimicrob Agents Chemother* 2014, 58(11), 6970-3.

International Search Report and Written Opinion Issued in Corresponding PCT Application No. PCT/us2016/048110, mailed Nov. 2, 2016.

Jacobsen, "Investigating the Humoral Immune Response in Chronic Venous Leg Ulcer Patients Colonised with Pseudomonas/ Aeruginosa," International Wound Journal, 20110.

Junka et al., "Efficacy of antiseptics containing povidone-iodine, octenidine dihydrochloride and ethacridine lactate against biofilm formed by Pseudomonas aeruginosa and *Staphylococcus aureus* measured with the novel biofilm-oriented antiseptics test" Int Wound J. 2014, 11(6), p. 730-4.

Matsumoto et al., "Duration of Absorption-Enhancing Effect of Sodium Octanoate, Sodium Hexanoate or Glyceryl-1-monooctanoate on Rectal Absorption of Gentamicin in Rabbits" *J.Pharmacobio-Dyn.* 1990, 13, 591-596.

Merck, Page, "Description of Skin Lesions," Merck Manual Professional Version, 2013 http://merckmanuals.com/professional/ dermatologic-disorders/approach-to-the- dermatologic-patient/ description-of-skin-lesions.

Mertz, "Cutaneous Biofilms: Friend or Foe?", *Wounds*, 15; 1-9, 2003.

Office Action issued in Corresponding Chinese Application No. 201680049463.4, dated Jun. 24, 2020 (English Translation provided).

Office Action issued in Corresponding Japanese Application No. 2018-510413, dated Jul. 20, 2020 (English Translation provided).

O'Meara et al., "Antibiotics and antiseptics for venous leg ulcers" *Cochrane Database of Systematic Reviews* 2014, Issue 1, Abstract only, pp. 1-4.

Research Council Meeting Abstract of Japan Society of Plastic and Reconstructive Surgery 2013, vol. 22, p. 85, O-2.

Sanchez, Jr. et al., "D-Amino Acids Enhance the Activity of Antimicrobials against Biofilms of Clinical Wound Isolates of *Staphylococcus aureus* and Pseudomonas aeruginosa" *Antimicrob Agents Chemother* 2014, 58(8), 4353-61.

Williamson, et al., "Heterogeneity in Pseudomonas Aeroginosa Biofilms Includes Expression of Ribosome Hibernation Factors in the Antibiotic-Tolerant Subpopulation and Hypoxia-Induced Stress Response in the Metabolically Active Population," *Journal of Bacteriology*, 2062-2073, 2012.

Zheng, et al., "Penetration of Rifampin Through *Staphylococcus epidermidis* Biofilms," *Antimicrobial Agents and Chemotherapy*, 900-903, 2002.

* cited by examiner

1

SYNERGISTIC ANTIBACTERIAL ACTIVITY OF MEDIUM POLARITY OILS IN COMBINATION WITH ANTIBACTERIAL AGENTS ON BACTERIAL BIOFILMS

CROSS-REFERENCE TO RELATED APPLICATION

This application is a continuation of U.S. patent application Ser. No. 17/545,409 filed Dec. 8, 2021, which is a continuation of U.S. patent application Ser. No. 16/529,303 filed Aug. 1, 2019 (now U.S. Pat. No. 11,197,476), which is a continuation of U.S. patent application Ser. No. 15/754,703 filed Feb. 23, 2018 (now abandoned), which is a national phase application under 35 U.S.C. § 371 of International Application No. PCT/US2016/048110 filed Aug. 23, 2016, which claims the benefit of U.S. Provisional Application No. 62/209,181 filed Aug. 24, 2015. The contents of the referenced applications are incorporated herein by reference.

FIELD OF THE INVENTION

The present invention generally relates to compositions having antibacterial activity against bacterial biofilms and use of such compositions for the reduction of bacteria in and/or elimination of bacterial biofilms on biological and non-biological surfaces. In particular, the compositions can include a combination of a medium polarity oil(s) and an antibacterial agent(s) and can be used to treat wounds, skin lesions, mucous membrane lesions, and other biological surfaces infected or contaminated with bacterial biofilms.

BACKGROUND OF THE INVENTION

Bacterial biofilms are populations of bacteria attached to a surface. Bacteria in a biofilm are frequently embedded within a self-produced matrix of an extracellular polymeric substance (EPS), which holds the bacteria together in a mass and firmly attaches the bacterial mass to the underlying surface. The bacterial biofilm EPS, which is often referred to as slime, is a polymeric conglomeration generally composed of extracellular DNA, proteins, polysaccharides, and various biopolymers. Biofilms can form on biological or non-biological surfaces and can be prevalent in both industrial and clinical settings.

Evidence has shown that biofilms constitute a significant threat to human health. Biofilms are responsible for more than 80% of microbial infections in the body ("Research on Microbial Biofilms", National Institutes of Health, PA Number: PA-03-047, Dec. 20, 2002). Biofilms are involved in health conditions such as urinary tract infections, cystitis, lung infections, skin infections, mucous membrane infections, sinus infections, ear infections, acne, dental caries, periodontitis, nosocomial infections, open wounds, and chronic wounds. Additionally, biofilms form on medical devices such as: urinary tract prostheses; urinary tract catheters; peritoneal membrane catheters, peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses; percutaneous sutures; and tracheal and ventilator tubing.

Bacteria growing in biofilms exhibit increased tolerance to antibiotics and antibacterial agents and are very difficult to substantially reduce or eliminate. Bacteria within biofilms have increased tolerance (up to 1000-fold higher) to antibacterial compounds than bacteria not within biofilms, even though these same bacteria are sensitive to these agents if grown under planktonic conditions ("Research on Microbial Biofilms", National Institutes of Health, PA Number: PA-03-047, Dec. 20, 2002). Bacteria grown in biofilms are also physiologically distinct from the same bacteria grown under planktonic conditions. The bacteria in biofilms are stratified into different metabolic states depending on where in the biofilm they reside and thus display different phenotypes compared to their free-living counterparts. Another theory behind the antimicrobial tolerance of bacteria in biofilms is the protective role of the EPS. The EPS can be visualized as a "mesh" or a network that can physically prevent foreign agents (i.e., antibacterial agents) from reaching the bacteria. Because of the EPS, altered metabolic states and acquired resistance factors, biofilms have a multifactorial tolerance to antibacterial agents and antibiotics. Moreover, most of the antibacterial formulations are water-based preparations, making it even harder for the antibacterial active to penetrate the biofilm network due to high surface tension of water molecules.

Wounds, mucous membrane lesions, and skin lesions are especially susceptible to bacterial infection. From a microbiological perspective, the primary function of normal, intact skin is to control microbial populations that live on the skin surface and to prevent underlying tissue from becoming colonized and invaded by potential pathogens. Exposure of subcutaneous tissue, such as a wound, mucous membrane lesion, or skin lesion, provides a moist, warm and nutritious environment that is conducive to microbial colonization and proliferation. Since wound colonization is mostly polymicrobial, involving numerous microorganisms that are potentially pathogenic, any wound, mucous membrane lesion, or skin lesion is at some risk of becoming infected.

Wounds often have multiple barriers to healing. Wound healing and infection is influenced by the relationship between the ability of bacteria to create a stable, prosperous community within a wound environment and the ability of the host to control the bacterial community. Since bacteria are rapidly able to form their own protective microenvironment, i.e., a biofilm, following their attachment to a surface, the ability of the host to control these organisms is likely to decrease as the biofilm community matures, ultimately affecting the ability of the wound to heal. Wounds in which healing is delayed, i.e., chronic wounds, are of particular concern with respect to biofilm formation. Some have linked biofilms to chronic wounds (Mertz, 2003, Wounds, 15: 1-9). Wounds such as diabetic foot ulcers, venous ulcers, arterial ulcers, decubitus ulcers, stasis ulcers, pressure ulcers, and burns are examples of wounds which may become chronic wounds. Bacterial biofilms in chronic wounds are generally not resolved by the host's immune system, and these biofilms have an increased tolerance to systemic and topical antibacterial/antibiotic agents. Accordingly, bacterial biofilm infections in chronic wounds are very difficult to substantially reduce or eliminate.

Particularly virulent organisms in wounds, mucous membrane lesions, and skin lesions are gram-positive bacteria such as *Staphylococcus* spp., *Streptococcus* spp., and *Enterococci* spp. Biofilms of *Staphylococcus aureus*, including resistant strains such as methicillin resistant *Staphylococcus aureus* (MRSA), have become increasingly problematic in wounds, skin lesions, and mucous membrane lesions. These organisms, especially MRSA, can reside in the anterior nares and cause lesions in the nose which can also spread to other parts of the body, causing skin lesions and mucous membrane lesions at those sites. The gram-negative bacteria *Pseudomonas aeruginosa* is also a particularly virulent organism in wounds (Bjarnsholt, 2008, Wound Repair and Regeneration; and Jacobsen, 2011, International Wound Journal).

In recent years, there have been numerous efforts to use various antibiotics and antibacterial agents for the treatment of mucous membrane lesions, skin lesions and chronic wounds, many of which are infected or contaminated with bacterial biofilms. These agents are of varying chemical compounds and include, among others, peptides such as vancomycin, and antibacterial agents such as mupirocin, iodine compounds, and silver/silver ions. However, many bacteria have become increasingly resistant to these compounds.

Thus, there is a need for safe and effective compositions which can reduce bacteria in or eliminate bacterial biofilms in wounds, mucous membrane lesions, and skin lesions, and on other biological and non-biological surfaces.

SUMMARY OF THE INVENTION

The present invention provides a solution to the aforementioned limitations and deficiencies in the art relating to bacterial biofilms. In particular, the solution is premised on the combination of at least one medium polarity oil having an octanol-water partition coefficient (log P) of 0.5 to 2.0 and at least one antibacterial agent in a composition. Surprisingly, this combination produces a synergistic antibacterial effect against bacterial biofilms. Stated another way, the synergistic effect means the total antibacterial activity against bacterial biofilms of the combination of the two components, i.e., the medium polarity oil plus the antibacterial agent, is greater than the sum of the antibacterial activity against biofilms of each component when measured separately. Without being bound by theory, it is postulated that the medium polarity oils, being dispersible in both oil and aqueous media, enhance penetration through the extracellular polymeric substance (EPS) produced by the biofilm bacteria, and increase the targeted delivery of the antibacterial agent. This combination of at least one medium polarity oil and at least one antibacterial agent can be used to produce a composition capable of: treating wounds, mucous membrane lesions, skin lesions, and/or other biological surfaces infected or contaminated with bacterial biofilms; reducing bacteria in and/or eliminating bacterial biofilms on biological surfaces; and/or reducing bacteria in and/or eliminating bacterial biofilms on non-biological surfaces such as on medical devices.

In one aspect of the invention, disclosed are methods of treating a wound, mucous membrane lesion, or skin lesion infected or contaminated with a bacterial biofilm, the method comprising topically administering to the wound, mucous membrane lesion, or skin lesion a composition comprising a combination of at least one medium polarity oil having an octanol-water partition coefficient (log P) of 0.5 to 2.0 and at least one antibacterial agent, wherein the combination of the at least one medium polarity oil and the at least one antibacterial agent exhibits synergistic antibacterial activity against the biofilm.

In another aspect of the invention, disclosed are methods of reducing bacteria in or eliminating a bacterial biofilm on a biological surface, the method comprising administering to the biological surface a composition comprising a combination of at least one medium polarity oil having an octanol-water partition coefficient (log P) of 0.5 to 2.0 and at least one antibacterial agent, wherein the combination of the at least one medium polarity oil and the at least one antibacterial agent exhibits synergistic antibacterial activity against the biofilm.

In still another aspect of the invention, disclosed are methods of reducing bacteria in or eliminating a bacterial biofilm on a non-biological surface, the method comprising administering to the non-biological surface a composition comprising a combination of at least one medium polarity oil having an octanol-water partition coefficient (log P) of 0.5 to 2.0 and at least one antibacterial agent, wherein the combination of the at least one medium polarity oil and the at least one antibacterial agent exhibits synergistic antibacterial activity against the biofilm.

In another aspect of the invention, disclosed are compositions suitable for application to biological and non-biological surfaces having bacterial biofilms, comprising a combination of at least one medium polarity oil having an octanol-water partition coefficient (log P) of 0.5 to 2.0 and at least one antibacterial agent, wherein the concentrations of the at least one medium polarity oil and the at least one antibacterial agent in the composition are at amounts that exhibit synergistic antibacterial activity against bacterial biofilms on biological and non-biological surfaces.

In still another aspect of the invention, disclosed are articles of manufacture comprising a surface coated with the compositions of the invention.

Also disclosed in the context of the present invention are embodiments 1 to 126.

Embodiment 1: A method of treating a wound, mucous membrane lesion, or skin lesion infected or contaminated with a bacterial biofilm, the method comprising topically administering to the wound, mucous membrane lesion, or skin lesion a composition comprising a combination of at least one medium polarity oil having an octanol-water partition coefficient (log P) of 0.5 to 2.0 and at least one antibacterial agent, wherein the combination of the at least one medium polarity oil and the at least one antibacterial agent exhibits synergistic antibacterial activity against the biofilm.

Embodiment 2: The method of embodiment 1, wherein the composition further comprises a carrier suitable for topical treatment.

Embodiment 3: The method of embodiments 1 or 2, wherein the antibacterial agent is a silver compound, an iodine compound, or an antibiotic.

Embodiment 4: The method of embodiments 1 or 2, wherein the antibacterial agent is not a C9-C12 aliphatic alcohol. In some aspects, the composition in embodiment 4 is free of/does not include a C9-C12 aliphatic alcohol.

Embodiment 5: The method of embodiments 1 or 2, wherein the antibacterial agent is a silver compound.

Embodiment 6: The method of embodiment 5, wherein the composition comprises a carrier suitable for topical treatment and the carrier is a ringing gel.

Embodiment 7: The method of embodiments 5 or 6, wherein the silver compound is silver sulfadiazine, silver nitrate, or silver chloride.

Embodiment 8: The method of embodiments 1 or 2, wherein the antibacterial agent is an iodine compound.

Embodiment 9: The method of embodiment 8, wherein the iodine compound is an iodophor.

Embodiment 10: The method of embodiment 9, wherein the iodophor is cadexomer-iodine.

Embodiment 11: The method of embodiment 9, wherein the iodophor is povidone-iodine.

Embodiment 12: The method of embodiments 1 or 2, wherein the antibacterial agent is an antibiotic.

Embodiment 13: The method of embodiment 12, wherein the composition comprises a carrier suitable for topical treatment and the carrier is a ringing gel.

Embodiment 14: The method of embodiments 12 or 13, wherein the antibiotic is an aminoglycoside antibiotic.

Embodiment 15: The method of embodiment 14, wherein the aminoglycoside antibiotic is gentamicin or gentamicin sulfate.

Embodiment 16: The method of embodiments 12 or 13, wherein the antibiotic is a polypeptide antibiotic.

Embodiment 17: The method of embodiment 16, wherein the polypeptide antibiotic is colistin or colistin sulfate.

Embodiment 18: The method of any one of embodiments 1 to 17, wherein the medium polarity oil is an ester.

Embodiment 19: The method of any one of embodiments 1 to 18, wherein the medium polarity oil is a fatty acid ester.

Embodiment 20: The method of any one of embodiments 1 to 19, wherein the medium polarity oil is a glyceryl ester.

Embodiment 21: The method of embodiment 20, wherein the glyceryl ester is glyceryl caprylate/caprate.

Embodiment 22: The method of embodiment 21, wherein the glyceryl caprylate/caprate is at a concentration of 7 to 40% w/w.

Embodiment 23: The method of embodiment 21, wherein the glyceryl caprylate/caprate is at a concentration of 7 to 15% w/w.

Embodiment 24: The method of any one of embodiments 1 to 23, wherein the bacterial biofilm is a gram-positive bacterial biofilm.

Embodiment 25: The method of embodiment 24, wherein the gram-positive bacterial biofilm is a *Staphylococcus* sp.

Embodiment 26: The method of embodiment 25, wherein the *Staphylococcus* sp. is *Staphylococcus aureus*.

Embodiment 27: The method of embodiment 26, wherein the *Staphylococcus* sp. is methicillin resistant *Staphylococcus aureus* (MRSA).

Embodiment 28: The method of any one of embodiments 1 to 23, wherein the bacterial biofilm is a gram-negative bacterial biofilm.

Embodiment 29: The method of embodiment 28, wherein the gram-negative bacterial biofilm is a *Pseudomonas* sp.

Embodiment 30: The method of embodiment 29, wherein the *Pseudomonas* sp. is *Pseudomonas aeruginosa*.

Embodiment 31: The method of any one of embodiments 1 to 30, wherein the wound is a chronic wound.

Embodiment 32: The method of embodiment 31, wherein the chronic wound is a diabetic foot ulcer, venous ulcer, arterial ulcer, decubitus ulcer, stasis ulcer, pressure ulcer, or burn.

Embodiment 33: The method of any one of embodiments 1 to 30, wherein the skin lesion or mucous membrane lesion, is a blister, ulceration, abrasion, wart, scrape, or infection.

Embodiment 34: The method of any one of embodiments 1 to 33, wherein the concentrations of the at least one medium polarity oil and the at least one antibacterial agent in the composition are at amounts that exhibit synergistic antibacterial activity against the biofilm.

Embodiment 35: The method of any one of embodiments 1 to 34, wherein the octanol-water partition coefficient (log P) is experimentally determined by the ASTM Standard Test Method for Partition Coefficient (N-Octanol/Water) Estimation by Liquid Chromatography, Designation E 1147-92.

Embodiment 36: A method of reducing bacteria in or eliminating a bacterial biofilm on a biological surface, the method comprising administering to the biological surface a composition comprising a combination of at least one medium polarity oil having an octanol-water partition coefficient (log P) of 0.5 to 2.0 and at least one antibacterial agent, wherein the combination of the at least one medium polarity oil and the at least one antibacterial agent exhibits synergistic antibacterial activity against the biofilm.

Embodiment 37: The method of embodiment 36, wherein the composition further comprises a carrier.

Embodiment 38: The method of embodiments 36 or 37, wherein the antibacterial compound is a silver compound, an iodine compound, or an antibiotic.

Embodiment 39: The method of embodiments 36 or 37, wherein the antibacterial agent is not a C9-C12 aliphatic alcohol. In some aspects, the composition in embodiment 39 is free of/does not include a C9-C12 aliphatic alcohol.

Embodiment 40: The method of embodiments 36 or 37, wherein the antibacterial agent is a silver compound.

Embodiment 41: The method of embodiment 40, wherein the composition comprises a carrier and the carrier is a ringing gel.

Embodiment 42: The method of embodiments 40 or 41, wherein the silver compound is silver sulfadiazine, silver nitrate, or silver chloride.

Embodiment 43: The method of embodiments 36 or 37, wherein the antibacterial agent is an iodine compound.

Embodiment 44: The method of embodiment 43, wherein the iodine compound is an iodophor.

Embodiment 45: The method of embodiment 44, wherein the iodophor is cadexomer-iodine.

Embodiment 46: The method of embodiment 44, wherein the iodophor is povidone-iodine.

Embodiment 47: The method of embodiments 36 or 37, wherein the antibacterial agent is an antibiotic.

Embodiment 48: The method of embodiment 47, wherein the composition comprises a carrier and the carrier is a ringing gel.

Embodiment 49: The method of embodiments 47 or 48, wherein the antibiotic is an aminoglycoside antibiotic.

Embodiment 50: The method of embodiment 49, wherein the aminoglycoside antibiotic is gentamicin or gentamicin sulfate.

Embodiment 51: The method of embodiments 47 or 48, wherein the antibiotic is a polypeptide antibiotic.

Embodiment 52: The method of embodiment 51, wherein the polypeptide antibiotic is colistin or colistin sulfate.

Embodiment 53: The method of any one of embodiments 36 to 52, wherein the medium polarity oil is an ester.

Embodiment 54: The method of any one of embodiments 36 to 53, wherein the medium polarity oil is a fatty acid ester.

Embodiment 55: The method of any one of embodiments 36 to 54, wherein the medium polarity oil is a glyceryl ester.

Embodiment 56: The method of embodiment 55, wherein the glyceryl ester is glyceryl caprylate/caprate.

Embodiment 57: The method of embodiment 56, wherein the glyceryl caprylate/caprate is at a concentration of 7 to 40% w/w.

Embodiment 58: The method of embodiment 56, wherein the glyceryl caprylate/caprate is at a concentration of 7 to 15% w/w.

Embodiment 59: The method of any one of embodiments 36 to 58, wherein the bacterial biofilm is a gram-positive bacterial biofilm.

Embodiment 60: The method of embodiment 59, wherein the gram-positive bacterial biofilm is a *Staphylococcus* sp.

Embodiment 61: The method of embodiment 60, wherein the *Staphylococcus* sp. is *Staphylococcus aureus*.

Embodiment 62: The method of embodiment 61, wherein the *Staphylococcus* sp. is methicillin resistant *Staphylococcus aureus* (MRSA).

Embodiment 63: The method of any one of embodiments 36 to 58, wherein the bacterial biofilm is a gram-negative bacterial biofilm.

Embodiment 64: The method of embodiment 63, wherein the gram-negative bacterial biofilm is a *Pseudomonas* sp.

Embodiment 65: The method of embodiment 64, wherein the *Pseudomonas* sp. is *Pseudomonas aeruginosa.*

Embodiment 66: The method of any one of embodiments 36 to 65, wherein the biological surface is a chronic wound.

Embodiment 67: The method of embodiment 66, wherein the chronic wound is a diabetic foot ulcer, venous ulcer, arterial ulcer, decubitus ulcer, stasis ulcer, pressure ulcer, or burn.

Embodiment 68: The method of any one of embodiments 36 to 65, wherein the biological surface is a skin lesion, or mucous membrane lesion.

Embodiment 69: The method of embodiment 68, wherein the skin lesion or mucous membrane lesion, is a blister, ulceration, abrasion, wart, scrape, or infection.

Embodiment 70: The method of any one of embodiments 36 to 69, wherein the concentrations of the at least one medium polarity oil and the at least one antibacterial agent in the composition are at amounts that exhibit synergistic antibacterial activity against the biofilm.

Embodiment 71: The method of any one of embodiments 36 to 70, wherein the octanol-water partition coefficient (log P) is experimentally determined by the ASTM Standard Test Method for Partition Coefficient (N-Octanol/Water) Estimation by Liquid Chromatography, Designation E 1147-92.

Embodiment 72: A method of reducing bacteria in or eliminating a bacterial biofilm on a non-biological surface, the method comprising administering to the non-biological surface a composition comprising a combination of at least one medium polarity oil having an octanol-water partition coefficient (log P) of 0.5 to 2.0 and at least one antibacterial agent, wherein the combination of the at least one medium polarity oil and the at least one antibacterial agent exhibits synergistic antibacterial activity against the biofilm.

Embodiment 73: The method of embodiment 72, wherein the composition further comprises a carrier suitable for application to a non-biological surface.

Embodiment 74: The method of embodiments 72 or 73, wherein the non-biological surface is a medical device.

Embodiment 75: The method of embodiment 74, wherein the medical device is a urinary tract prosthesis, urinary tract catheter, peritoneal membrane catheter, peritoneal dialysis catheter, indwelling catheter for hemodialysis, indwelling catheter for administration of chemotherapeutic agents, cardiac implant, pacemaker, prosthetic heart valve, ventricular assist device, synthetic vascular graft, synthetic vascular stent, prosthesis, percutaneous suture, tracheal tubing, or ventilator tubing.

Embodiment 76: The method of any one of embodiments 72 to 75, wherein the concentrations of the at least one medium polarity oil and the at least one antibacterial agent in the composition are at amounts that exhibit synergistic antibacterial activity against the biofilm.

Embodiment 77: The method of any one of embodiments 72 to 76, wherein the octanol-water partition coefficient (log P) is experimentally determined by the ASTM Standard Test Method for Partition Coefficient (N-Octanol/Water) Estimation by Liquid Chromatography, Designation E 1147-92.

Embodiment 78: A composition comprising a combination of at least one medium polarity oil having an octanol-water partition coefficient (log P) of 0.5 to 2.0 and at least one antibacterial agent, wherein the concentrations of the at least one medium polarity oil and the at least one antibacterial agent in the composition are at amounts that exhibit synergistic antibacterial activity against bacterial biofilms on biological and non-biological surfaces.

Embodiment 79: The composition of embodiment 78, wherein the composition further comprises a carrier.

Embodiment 80: The composition of embodiment 79, wherein the carrier is a carrier suitable for application to a non-biological surface.

Embodiment 81: The composition of embodiment 79, wherein the carrier is a pharmaceutical carrier.

Embodiment 82: The composition of embodiment 81, wherein the pharmaceutical carrier is a lotion, solution, suspension, liquid, emulsion, cream, gel, ringing gel, ointment, paste, aerosol spray, aerosol foam, non-aerosol spray, non-aerosol foam, film, or sheet.

Embodiment 83: The composition of any one of embodiments 78 to 82, wherein the antibacterial agent is a silver compound, an iodine compound, or an antibiotic.

Embodiment 84: The composition of any one of embodiments 78 to 82, wherein the antibacterial agent is not a C9-C12 aliphatic alcohol. In some aspects, the composition in embodiment 84 is free of/does not include a C9-C12 aliphatic alcohol.

Embodiment 85: The composition of any one of embodiments 78 to 82, wherein the antibacterial agent is a silver compound.

Embodiment 86: The composition of embodiment 85, wherein the composition comprises a carrier and the carrier is a ringing gel.

Embodiment 87: The composition of embodiments 85 or 86, wherein the silver compound is silver sulfadiazine, silver nitrate, or silver chloride.

Embodiment 88: The composition of any of embodiments 85 to 87, wherein the silver compound is at a concentration of 0.1 to 5% w/w.

Embodiment 89: The composition of any of embodiments 78 to 82, wherein the antibacterial agent is an iodine compound.

Embodiment 90: The composition of embodiment 89, wherein the iodine compound is an iodophor.

Embodiment 91: The composition of embodiment 90, wherein the iodophor is cadexomer-iodine.

Embodiment 92: The composition of embodiment 91, wherein the cadexomer-iodine is at a concentration of 40 to 60% w/w.

Embodiment 93: The composition of embodiment 90, wherein the iodophor is povidone-iodine.

Embodiment 94: The composition of embodiment 93, wherein the povidone-iodine is at a concentration of 1 to 20% w/w.

Embodiment 95: The composition of any one of embodiments 78 to 82, wherein the antibacterial agent is an antibiotic.

Embodiment 96: The composition of embodiment 95, wherein the composition comprises a carrier and the carrier is a ringing gel.

Embodiment 97: The composition of embodiments 95 or 96, wherein the antibiotic is an aminoglycoside antibiotic.

Embodiment 98: The composition of embodiment 97, wherein the aminoglycoside antibiotic is gentamicin or gentamicin sulfate.

Embodiment 99: The composition of embodiment 98, wherein the gentamicin or gentamicin sulfate is at a concentration of 0.1 to 5% w/w.

Embodiment 100: The composition of embodiments 95 or 96, wherein the antibiotic is a polypeptide antibiotic.

Embodiment 101: The composition of embodiment 100, wherein the polypeptide antibiotic is colistin or colistin sulfate.

Embodiment 102: The composition of embodiment 101, wherein the concentration of colistin or colistin sulfate is 0.01 to 2% w/w.

Embodiment 103: The composition of any one of embodiments 78 to 102, wherein the medium polarity oil is an ester.

Embodiment 104: The composition of any one of embodiments 78 to 103, wherein the medium polarity oil is a fatty acid ester.

Embodiment 105: The composition of any one of embodiments 78 to 104, wherein the medium polarity oil is a glyceryl ester.

Embodiment 106: The composition of embodiment 105, wherein the glyceryl ester is glyceryl caprylate/caprate.

Embodiment 107: The composition of embodiment 106, wherein the glyceryl caprylate/caprate is at a concentration of 7 to 40% w/w.

Embodiment 108: The composition of embodiment 106, wherein the glyceryl caprylate/caprate is at a concentration of 7 to 15% w/w.

Embodiment 109: The composition of any one of embodiments 78 to 108, wherein the bacterial biofilm is a gram-positive bacterial biofilm.

Embodiment 110: The composition of embodiment 109, wherein the gram-positive bacterial biofilm is a *Staphylococcus* sp.

Embodiment 111: The composition of embodiment 110, wherein the *Staphylococcus* sp. is *Staphylococcus aureus*.

Embodiment 112: The composition of embodiment 111, wherein the *Staphylococcus* sp. is methicillin resistant *Staphylococcus aureus* (MRSA).

Embodiment 113: The composition of any one of embodiments 78 to 108, wherein the bacterial biofilm is a gram-negative bacterial biofilm.

Embodiment 114: The composition of embodiment 113, wherein the gram-negative bacterial biofilm is a *Pseudomonas* sp.

Embodiment 115: The composition of embodiment 114, wherein the *Pseudomonas* sp. is *Pseudomonas aeruginosa*.

Embodiment 116: The composition of any one of embodiments 78 to 115, wherein the biological surface is a chronic wound.

Embodiment 117: The composition of embodiment 116, wherein the chronic wound is a diabetic foot ulcer, venous ulcer, arterial ulcer, decubitus ulcer, stasis ulcer, pressure ulcer, or burn.

Embodiment 118: The composition of any one of embodiments 78 to 115, wherein the biological surface is a skin lesion, or mucous membrane lesion.

Embodiment 119: The composition of embodiment 118, wherein the skin lesion or mucous membrane lesion, is a blister, ulceration, abrasion, wart, scrape, or infection.

Embodiment 120: The composition of any one of embodiments 78 to 119, wherein the octanol-water partition coefficient (log P) is experimentally determined by the ASTM Standard Test Method for Partition Coefficient (N-Octanol/Water) Estimation by Liquid Chromatography, Designation E 1147-92.

Embodiment 121: An article of manufacture comprising a surface coated with the composition of any one of embodiments 78 to 115.

Embodiment 122: The article of manufacture of embodiment 121, wherein the article of manufacture is a medical device.

Embodiment 123: The article of manufacture of embodiment 121, wherein the medical device is a urinary tract prosthesis, urinary tract catheter, peritoneal membrane catheter, peritoneal dialysis catheter, indwelling catheter for hemodialysis, indwelling catheter for administration of chemotherapeutic agents, cardiac implant, pacemaker, prosthetic heart valve, ventricular assist device, synthetic vascular graft, synthetic vascular stent, prosthesis, percutaneous suture, tracheal tubing, or ventilator tubing.

Embodiment 124: The article of manufacture of any one of embodiments 121 to 123, wherein a biofilm is not present on the coated surface.

Embodiment 125: The article of manufacture of any one of embodiments 121 to 123, wherein a biofilm is present on the coated surface.

Embodiment 126: The article of manufacture of any one of embodiments 121 to 125, wherein the octanol-water partition coefficient (log P) is experimentally determined by the ASTM Standard Test Method for Partition Coefficient (N-Octanol/Water) Estimation by Liquid Chromatography, Designation E 1147-92.

Unless otherwise specified, the percent values expressed herein are weight by weight and are in relation to the weight of the total composition. By way of example, 10 grams of an ingredient in 100 grams of a composition that includes the 10 grams of the ingredient is 10 wt. % of the ingredient in the composition.

The term "reduce," "reduced," "reducing," or "reduction" in the context of a bacterial biofilm means a reduction in the count of bacteria present in the biofilm.

The term "treat," "treated," or "treating," in the context of treating a bacterial biofilm on a biological surface, or treating a mucous membrane lesion, a wound, or a skin lesion, means any measurable decrease or complete elimination of the bacterial biofilm, and/or a therapeutic improvement of the mucous membrane lesion, wound, or skin lesion.

The term "effective," in the context of treating a bacterial biofilm or treating a wound, mucous membrane lesion, or skin lesion means adequate to accomplish a desired, expected, or intended result, including a therapeutic improvement.

The term "eliminate," "eliminated," "eliminating," or "elimination" in the context of a bacterial biofilm means total eradication of the bacteria present in the biofilm.

The term "wound" as used herein means an external wound of the skin or mucous membranes and includes chronic and acute wounds.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the word "a" or "an" when used in conjunction with the terms "comprising," "having," "including," or "containing" (or any variations of these words) may mean "one," but it is also consistent with the meaning of "one or more," "at least one," and "one or more than one."

The compositions and methods for their use can "comprise," "consist essentially of," or "consist of" any of the ingredients or steps disclosed throughout the specification.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
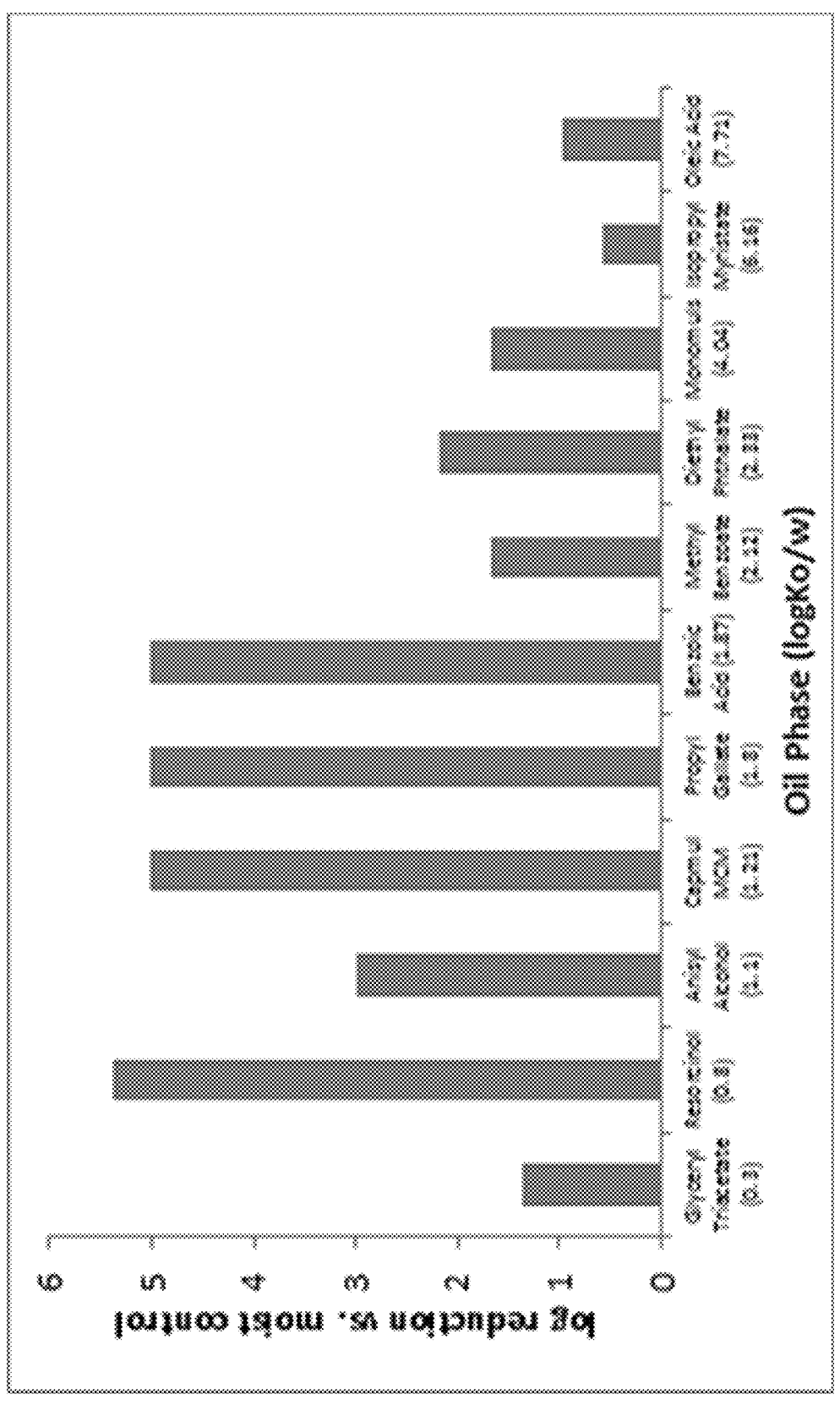
FIG. 1 shows the log reduction of bacteria in an in-vitro *S. aureus* biofilm model after treatment with various oils of various polarity vs. moist control.

The present invention relates to methods and compositions useful for the reduction of bacteria in and/or elimination of bacterial biofilms on surfaces. In particular, the present invention provides compositions which exhibit activity against bacterial biofilms, and methods of using the same to treat biological and non-biological surfaces infected or contaminated with bacterial biofilms by reducing bacteria in or eliminating the bacterial biofilm. In one aspect, the present invention relates to methods and compositions useful for the treatment of wounds, skin lesions, mucous membrane lesions, and other biological surfaces infected or contaminated with bacterial biofilms. In another aspect, the present invention relates to methods and compositions useful for the reduction of bacteria in and/or elimination of bacterial biofilms on non-biological surfaces such as medical devices.

The compositions of the present invention comprise at least one medium polarity oil and at least one antibacterial agent. Surprisingly, the combination of at least one medium polarity oil and at least one antibacterial agent produces a synergistic antibacterial effect against bacterial biofilms. Stated another way, the total antibacterial activity against bacterial biofilms of the combination of the two components, i.e., the medium polarity oil plus the antibacterial agent, is greater than the sum of the antibacterial activity against biofilms of each component when measured separately.

I. Compositions

The compositions of the present invention comprise at least one medium polarity oil and at least one antibacterial agent, both of which are described below in a non-limiting manner. The concentrations of the at least one medium polarity oil and the at least one antibacterial agent in the compositions are at an amount that exhibits synergistic antibacterial activity against bacterial biofilms.

The compositions of the invention can also include an acceptable carrier such as a carrier suitable for topical products or a carrier suitable for application to a non-biological surface, such as a medical device. The carrier may also be a pharmaceutical carrier suitable for application to biological surfaces including topical surfaces. The compositions of the present invention can comprise carriers suitable for topical treatment of skin, mucous membranes, and wounds. Non-limiting examples of carriers include lotions, solutions, suspensions, liquids, emulsions, creams, gels, ringing gels, ointments, pastes, aerosol sprays, aerosol foams, non-aerosol sprays, non-aerosol foams, films, powders, and sheets. The compositions can be impregnated in gauzes, bandages, or other wound dressing materials. Non-limiting examples of carriers suitable for topical treatment of skin, mucous membranes and wounds include those disclosed in U.S. Pat. No. 6,399,092, herein incorporated by reference. Other examples of carriers suitable for topical treatment of skin, mucous membranes, and wounds include polyethylene glycol ointments. Especially suitable carriers include ringing gels, which are viscous microemulsions that are generally transparent, and exhibit a ringing phenomenon when excited to mechanical vibrations. Ringing gels can be O/W or W/O. Ringing gels are inherently viscous and do not need the addition of thickening agents in order to provide a viscous composition. Formulations of ringing gels are known in the art. An example of a formulation of a ringing gel carrier comprises water, a glyceryl ester such as CAPMUL® MCM, and a poloxamer such as poloxamer-407. Ringing gels are especially suitable for topical applications, such as to wounds or skin, in that the viscous composition will not run out of a wound or run off the skin when applied. An additional benefit of the use of ringing gel carriers for the present invention is that since thickening agents are not needed, there is less chance of ingredients interfering with the synergistic activity of the composition and less chance for irritation when applied to biological surfaces such as skin or wounds. Viscosity values for ringing gel carriers of the present invention can be at least 6250 cps, or at least 12,500 cps, or at least 25,000 cps, or at least 50,000 cps, or at least 60,000 cps, or at least 75,000 cps, or 6250 cps to 125,000 cps, or 12,500 cps to 125,000 cps, or 25,000 cps to 125,000 cps, or 50,000 cps to 125,000 cps, or 60,000 cps to 125,000 cps, or 75,000 cps to 125,000 cps when measured with a Brookfield viscometer with a small sample adapter, spindle #14, 6R chamber, at room temperature (22°-25° C.), at 10 rpm for 1 minute.

The compositions of the invention may further comprise functional ingredients suitable for use in compositions for application to biological surfaces or non-biological surfaces. Non-limiting examples include absorbents, super absorbents, antibacterial agents, antioxidants, binders, buffering agents, bulking agents, chelating agents, colorants, biocides, deodorant agents, emulsion stabilizers, film formers, fragrance ingredients, humectants, lytic agents, enzymatic agents, opacifying agents, oxidizing agents, pH adjusters, plasticizers, preservatives, reducing agents, emollient skin conditioning agents, humectant skin conditioning agents, moisturizers, surfactants, emulsifying agents, cleansing agents, foaming agents, hydrotopes, solvents, suspending agents, viscosity control agents (rheology modifiers), viscosity increasing agents (thickeners), and propellants. Listings and monographs of suitable functional ingredients are disclosed in McCutcheon's Vol. 1 Emulsifiers & Detergents, and Vol. 2 Functional Materials, 2001, herein incorporated by reference.

The compositions of the invention can further comprise pharmaceutically active ingredients, cosmetically active ingredients, and vulnerary agents suitable for topical use. The compositions can be sterile or preserved with preservatives. In some embodiments, the compositions do not include C9-C12 aliphatic alcohols. In some embodiments, the compositions do not include organic acids. In some embodiments, the compositions do not include glyceryl monolaurate.

The compositions of the present invention may be packaged in any suitable package configuration. Non-limiting examples include bottles, lotion pumps, toddles, tubes, jars, non-aerosol pump sprayers, aerosol containers, pouches, and packets. The packages may be configured for single-use or multiple-use administration.

A. Medium Polarity Oils

The compositions of the invention comprise at least one medium polarity oil with an octanol-water partition coefficient (log P) of 0.5 to 2.0. In some embodiments the octanol-water partition coefficient (log P) is 0.7 to 1.9. In other embodiments, the octanol-water partition coefficient (log P) is 0.7 to 1.8. The octanol-water partition coefficient, "$K_{ow}$", also represented as "P", is the ratio of the equilibrium molar concentration of a chemical in n-octanol and water, in dilute solution at a given temperature. The value is usually expressed as the decadic logarithm of this coefficient represented as, "log $K_{ow}$", also represented as "log P". The octanol-water partition coefficient is a measure of the hydrophobicity and hydrophilicity of a substance. Non-polar (hydrophobic) compounds have a high log P whereas polar (hydrophilic) compounds have a low log P. Medium polarity compounds have a log P in between non-polar and polar compounds. For the purposes of the present invention, medium polarity compounds have a log P of 0.5 to 2.0, or 0.7 to 1.9, or 0.7 to 1.8. For the purposes of the present invention, the term "medium polarity oil" is used interchangeably with the term "medium polarity compound," and means a compound that is liquid or solid at room temperature having a log P of 0.5 to 2.0, or 0.7 to 1.9, or 0.7 to 1.8.

Many methods exist for determining the octanol-water partition coefficient of a substance. However, for purposes of the present invention, the experimental determination of an octanol-water partition coefficient value utilizes a reverse phase (RP) HPLC method. One such method is described in the ASTM Standard Test Method for Partition Coefficient (N-Octanol/Water) Estimation by Liquid Chromatography, Designation E 1147-92 (Reapproved 2005), herein incorporated by reference. The methodology of the ASTM method is as follows. The test substance (solute) is injected onto a liquid chromatograph column containing a solid-phase support onto which a commercially available long-chain hydrocarbon (for example C8 or C18) has been bonded. Chemicals injected onto such a column move along it by partitioning between the mobile phase and the stationary hydrocarbon phase. A methanol/water solvent system is typically used to elute the solute which is subsequently analyzed using an ultraviolet/visible absorption detector, refractive index detector, electro-chemical detector, or other appropriate detector. If the test substance is not amenable to detection by the available LC detectors, the analyst may collect fractions of the column effluent and analyze for the test substance using gas chromatography, liquid scintillation, or other appropriate technique. The $K_{ow}$ of the test compound is estimated from a linear regression equation developed from a plot of log ($t_R$-$t_o$) versus log $K_{ow}$, using data determined in a calibration step that involves injecting into the chromatograph a mixture of reference chemicals. A calibration graph of log ($t_R$-$t_o$) versus log $K_{ow}$ is developed for a number of reference compounds (typically between 5 and 10) which are structurally similar to the test chemical. Lists of values of measured log $K_{ow}$ are available for many chemicals. If data on the partition coefficients of structurally related compounds are not available, a more general calibration graph can be developed using other reference compounds. The reference compound or test chemical retention time ($t_R$) is the time from sample injection to maximum concentration (peak height) of eluted reference compound or test chemical. The internal standard retention time ($t_o$) is the time from sample injection to the maximum concentration (peak height) of the eluted internal standard. The normalized retention time for each unknown is $t_R$-$t_o$. The results are calculated and reported as follows. Using the plot of log ($t_R$-$t_o$) versus log $K_{ow}$ for the reference compounds, compute the linear regression equation of the form log $K_{ow}$=a log ($t_R$-$t_o$)+b, where a and b are the slope and intercept, respectively. From the standard curve or regression equation, calculate an estimated log $K_{ow}$ for the test compound corresponding to the measured log ($t_R$-$t_o$). Report the standard curve of log ($t_R$-$t_o$) versus log $K_{ow}$ for each buffered or unbuffered eluent, or report the regression equation in the form of log $K_{ow}$=a log ($t_R$-$t_o$)+b. In some embodiments, the octanol-water partition coefficient (log P) is experimentally determined by the ASTM Standard Test Method for Partition Coefficient (N-Octanol/Water) Estimation by Liquid Chromatography, Designation E 1147-92.

Alternatively, for purposes of the present invention, the octanol-water partition coefficient values (log P) may be obtained from the "preferred" or "good" values defined and listed in Exploring QSAR, Vol. 1 Fundamentals and Applications in Chemistry and Biology, and Vol. 2, Hydrophobic, Electronic, and Steric Constants, Corwin Hansch, ACS Professional Reference Book, 1995, herein incorporated by reference.

The inventors determined experimentally that medium polarity oils. i.e., oils with a log P of 0.5 to 2.0, exhibited some antibacterial activity against biofilms, whereas non-polar and polar oils generally did not exhibit very much antibacterial activity against biofilms. The log reduction of bacteria in an in-vitro S. aureus biofilm model after treatment with various oils of various polarity vs. moist control is shown in FIG. 1. As can be seen in FIG. 1, the compounds having a log P outside the range of 0.5 to 2.0 did not exhibit very much antimicrobial activity against biofilms compared to the compounds having a log P within the range of 0.5 to 2.0. The compounds having a log P outside the range of 0.5 to 2.0 include glyceryl triacetate, methyl benzoate, diethyl acetate, MONOMULS® (glyceryl monolaurate), isopropyl myristate, and oleic acid. Compounds having a log P within the range of 0.5 to 2.0 include resorcinol, anisyl alcohol, benzoic acid, benzyl alcohol, ethyl acetate, ethyl gallate, phenoxyethanol, phenyethanol, propyl gallate, and glyceryl caprylate/caprate, and are shown in Table 1 below.

In some embodiments, the medium polarity oils are esters. Esters are the covalent compounds formed between acids and alcohols. In other embodiments, the medium polarity oils are fatty acid esters which are compounds formed between fatty acids and alcohols. In still other embodiments, the medium polarity oils are glyceryl esters. Glyceryl esters are primarily fatty acid mono-, di-, and/or tri-glycerides. One such glyceryl ester is glyceryl caprylate/caprate. Glyceryl caprylate/caprate is available from the Abitec Company under the trade name CAPMUL® MCM, NF and from Sasol Olefins & Surfactants GmbH under the trade name IMWITOR 742. Glyceryl caprylate/caprate is also known by its synonyms: caprylic/capric glycerides (INCI name); mono- and di-glycerides (NF name); glycerol monocaprylocaprate; medium chain mono- & diglycerides; glycerides C8-10 mono- di- tri-; and glyceryl mono- & dicaprylo/caprate. Glyceryl caprylate/caprate has an octanol-water partition coefficient value of 1.21 as determined experimentally by the ASTM method mentioned above. Glyceryl caprylate/caprate is a mono-diglyceride of medium chain fatty acids (mainly caprylic and capric). It is a mixture of monoacylglycerols, mainly mono-O-octanoylglycerol and mono-O-decanolyglycerol, containing variable quantities of di- and triacylglycerols. It is obtained by direct esterification of glycerol with caprylic (octanoic) and capric (decanoic) acids. CAPMUL MCM, NF and IMWITOR 742 meet the requirements of the USP/NF under the NF monograph for "mono- and di-glycerides."

TABLE 1

| Medium Polarity Oil | Log P value |
| --- | --- |
| Resorcinol | 0.80* |
| Anisyl Alcohol | 1.10* |
| Benzoic Acid | 1.87* |
| Benzyl Alcohol | 1.10* |
| Ethyl Acetate | 0.73* |
| Ethyl Gallate | 1.30* |
| Phenylethanol | 1.42* |
| Phenoxyethanol | 1.16* |
| Propyl Gallate | 1.80* |
| Glyceryl Caprate/Caprylate | 1.21** |

*value obtained from Exploring QSAR, Vol. 2
**value determined experimentally by ASTM method The concentrations of the medium polarity oil and the antibacterial agent components in the compositions are at amounts that exhibit synergistic antibacterial activity against bacterial biofilms. The concentration of the medium polarity oil in the compositions can vary with different oils, but generally can be 1 to 50% w/w, or 1 to 40% w/w, or 1 to 30% w/w, or 1 to 25% w/w, or 1 to 20% w/w, or 1 to 10% w/w, or 5 to 10% w/w, or 5 to 11% w/w, or 5 to 12% w/w, or 5 to 15% w/w, or 5 to 25% w/w, or 5 to 30% w/w, or 5 to 40%, w/w, or 5 to 50% w/w, or 6 to 50% w/w, or 6 to 40% w/w, or 6 to 30% w/w, or 6 to 25% w/w, or 6 to 20% w/w, or 6 to 15% w/w, or 6 to 12% w/w, or 6 to 11% w/w, or 6 to 10% w/w, or 7 to 50% w/w, or 7 to 40% w/w, or 7 to 30% w/w, or 7 to 25% w/w, or 7 to 20% w/w, or 7 to 15% w/w, or 7 to 12% w/w, or 7 to 11% w/w, or 7 to 10% w/w, or 8 to 50% w/w, or 8 to 40% w/w, or 8 to 30% w/w, or 8 to 25% w/w, or 8 to 20% w/w, or 8 to 15% w/w, or 8 to 12% w/w, or 8 to 11% w/w, or 8 to 10% w/w, or 9 to 50% w/w, or 9 to 40% w/w, or 9 to 30% w/w, or 9 to 25% w/w, or 9 to 20% w/w, or 9 to 15% w/w, or 9 to 12% w/w, or 9 to 11% w/w, or 9 to 10% w/w, or at least 5% w/w, or at least 6% w/w, or at least 7% w/w, or at least 8% w/w, or at least 9% w/w, or at least 10% w/w. In some embodiments, the medium polarity oil is an ester, fatty acid ester, or glyceryl ester and the concentration in the composition is 6 to 50% w/w, or 6 to 40% w/w, or 6 to 30% w/w, or 6 to 25% w/w, or 6 to 20% w/w, or 6 to 15% w/w, or 6 to 12% w/w, or 6 to 11% w/w, or 6 to 10% w/w, or 7 to 50% w/w, or 7 to 40% w/w, or 7 to 30% w/w, or 7 to 25% w/w, or 7 to 20% w/w, or 7 to 15% w/w, or 7 to 12% w/w, or 7 to 11% w/w, or 7 to 10% w/w, or 8 to 50% w/w, or 8 to 40% w/w, or 8 to 30% w/w, or 8 to 25% w/w, or 8 to 20% w/w, or 8 to 15% w/w, or 8 to 12% w/w, or 8 to 11% w/w, or 8 to 10% w/w, or 9 to 50% w/w, or 9 to 40% w/w, or 9 to 30% w/w, or 9 to 25% w/w, or 9 to 20% w/w, or 9 to 15% w/w, or 9 to 12% w/w, or 9 to 11% w/w, or 9 to 10% w/w, or at least 6% w/w, or at least 7% w/w, or at least 8% w/w, or at least 9% w/w, or at least 10% w/w. In some embodiments, the medium polarity oil is glyceryl caprate/caprylate and the concentration in the composition is 6 to 50% w/w, or 6 to 40% w/w, or 6 to 30% w/w, or 6 to 25% w/w, or 6 to 20% w/w, or 6 to 15% w/w, or 6 to 12% w/w, or 6 to 11% w/w, or 6 to 10% w/w, or 7 to 50% w/w, or 7 to 40% w/w, or 7 to 30% w/w, or 7 to 25% w/w, or 7 to 20% w/w, or 7 to 15% w/w, or 7 to 12% w/w, or 7 to 11% w/w, or 7 to 10% w/w, or 8 to 50% w/w, or 8 to 40% w/w, or 8 to 30% w/w, or 8 to 25% w/w, or 8 to 20% w/w, or 8 to 15% w/w, or 8 to 12% w/w, or 8 to 11% w/w, or 8 to 10% w/w, or 9 to 50% w/w, or 9 to 40% w/w, or 9 to 30% w/w, or 9 to 25% w/w, or 9 to 20% w/w, or 9 to 15% w/w, or 9 to 12% w/w, or 9 to 11% w/w, or 9 to 10% w/w, or at least 6% w/w, or at least 7% w/w, or at least 8% w/w, or at least 9% w/w, or at least 10% w/w.

B. Antibacterial Agents

The compositions of the invention comprise at least one antibacterial agent. Various antibacterial agents are suitable for use with the present invention. Suitable antibacterial agents include silver compounds such as the following non-limiting examples: elemental silver, silver nanoparticles, silver zeolite, silver sulfadiazine, ionized silver, and silver salts such as silver chloride and silver nitrate. Other suitable antibacterial agents include iodine compounds such as the following non-limiting examples: iodine, tincture of iodine, Lugol's iodine solution, iodides, iodine topical solution, iodine complexed with phosphate ester of alkylaryloxy polyethylene, iodoquinol, undecoylium chloride-iodine, nonylphenoxypolyethanol-iodine complex, and iodophors such as povidone-iodine (PVP-iodine), polyvinyl alcohol-iodine, polyvinyl oxazolidone-iodine, polyvinyl imidazole-iodine, polyvinyl morpholone-iodine, and polyvinyl caprolactam-iodine, nonylphenolethoxylate-iodine, soluble starch-iodine, betacyclodextrin-iodine, polyoxyethylenepolyoxypropylene condensate-iodine, ethoxylated linear alcohol-iodine, and cadexomer-iodine. Additional non-limiting examples of suitable antibacterial agents include: quaternary ammonium compounds such as benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide; chlorine containing compounds such as sodium hypochlorite, calcium hypochlorite, and chlorine dioxide; hydrogen peroxide; benzoic acid and its salts; benzoyl peroxide; benzyl alcohol; bispyrithione salts; boric acid; camphorated metacresol; camphorated phenol; chlorobutanol; cloflucarban; dapsone; dehydroacetic acid and its salts; ethyl alcohol; hexachlorophene; hexitidine; hexylresorcinol; hydroxybenzoic acid and its salts; isopropyl alcohol; mafenide acetate; magnesium pyrithione; merbromin; mercufenol chloride; methylparaben; metronidazole and its derivatives; mupirocin and its salts; nitrofurazone; n-Propanol; organic peroxides; p-chloro-m-xylenol; phenol; phenoxyethanol; phenyl alcohol; phenyl ethyl alcohol; selenium sulfide; sodium oxychlorosene; sodium sulfacetamide; sorbic acid and its salts; sulfur; tetrachlorosalicylanilide; thymol; tribromsalan; triclocarban; triclosan; and zinc pyrithione.

Antibiotics and antibacterial peptides are also suitable antibacterial agents. Suitable antibiotics include polypeptide antibiotics, examples of which are colistin (polymyxin E), colistin A (polymyxin E1), colistin B (polymyxin E2), colistin sulfate, colistimethate sodium, actinomycin, bacitracin, and polymyxin B. Other suitable antibiotics include aminoglycoside antibiotics, examples of which are gentamicin, gentamicin sulfate, neomycin, kanamycin, and tobramycin. Other suitable antibiotics include glycopeptide antibiotics, examples of which are vancomycin, teicoplanin, telavancin, ramoplanin, decaplanin, and bleomycin. Other suitable antibiotics include macrolide antibiotics, examples of which are azithromycin, clarithromycin, erythromycin, fidaxomicin, telithromycin, spiramycin, and troleandomycin. Other suitable antibiotics include mupirocin, calcium mupirocin, and retapamulin.

In some embodiments, the antibacterial agent is an iodine compound. In other embodiments, the iodine compound is an iodophor. In still other embodiments, the iodophor is cadexomer-iodine or povidone-iodine. In some embodiments, the cadexomer-iodine is at a concentration in the composition of 40 to 60% w/w, or 40 to 50% w/w, or 45 to 55% w/w, or 50 to 60% w/w, or about 50% w/w. In some embodiments, the povidone-iodine is at a concentration in the compositions of 1 to 25% w/w, or 1 to 20% w/w, or 1 to 15% w/w, or 3 to 15% w/w, or 5 to 10% w/w, or about 5% w/w, or about 10% w/w. In some embodiments, the antibacterial agent is a silver compound. In other embodiments, the silver compound is silver sulfadiazine, silver nitrate, or silver chloride. In some embodiments, the silver sulfadiazine is at a concentration in the composition of 0.1 to 10% w/w, or 0.1 to 5% w/w, or 0.1 to 2% w/w, or 0.1 to 1.5%, or 0.5 to 5% w/w, or 0.5 to 2% w/w, or 0.5 to 1.5% w/w, or 0.5 to 1% w/w, or 0.1 to 1% w/w, or 1 to 5% w/w, or about 0.5% w/w, or about 1% w/w. In some embodiments, the silver nitrate is at a concentration in the composition of 0.1 to 10% w/w, or 0.1 to 5% w/w, or 0.1 to 2% w/w, or 0.1 to 1.5%, or 0.5 to 1% w/w, or 0.5 to 5% w/w, or 0.5 to 2% w/w, or 0.5 to 1.5% w/w, or 0.1 to 1% w/w, or 1 to 5% w/w, or about 0.5% w/w, or about 1% w/w. In some embodiments, the silver chloride is at a concentration in the composition of 0.1 to 10% w/w, or 0.1 to 5% w/w, or 0.1 to 2% w/w, or 0.1 to 1.5%, or 0.5 to 1% w/w, or 0.5 to 5% w/w, or 0.5 to 2% w/w, or 0.5 to 1.5% w/w, or 0.1 to 1% w/w, or 1 to 5% w/w, or about 0.5% w/w, or about 1% w/w. In some embodiments, the antibacterial agent is an antibiotic. In other embodiments, the antibiotic is an aminoglycoside antibiotic. In still other embodiments, the aminoglycoside antibiotic is gentamicin or gentamicin sulfate. In some embodiments, the gentamicin or gentamicin sulfate is at a concentration in the composition of 0.1 to 10% w/w, or 0.1 to 5% w/w, or 0.1 to 2% w/w, or 0.1 to 1% w/w, or 0.5 to 5% w/w, or 0.5 to 2% w/w, or 0.5 to 1% w/w, or 0.5 to 0.7% w/w, or 0.7 to 1% w/w, or about 0.7% w/w. In other embodiments, the antibiotic is a polypeptide antibiotic. In still other embodiments, the polypeptide antibiotic is colistin or colistin sulfate. In some embodiments, the colistin or colistin sulfate is at a concentration in the composition of 0.01 to 5% w/w, or 0.01 to 2% w/w, or 0.01 to 1% w/w, or 0.01 to 0.5% w/w, or 0.01 to 0.2% w/w, or 0.05 to 1% w/w, or 0.05 to 0.5% w/w, or 0.05 to 0.2% w/w, or 0.05 to 0.15% w/w or about 0.1% w/w. In some embodiments, the antibacterial agent is not chlorhexidine gluconate.

The concentrations of the medium polarity oil and the antibacterial agent components in the compositions are at amounts that exhibit synergistic antibacterial activity against bacterial biofilms. The concentration of the antibacterial agent in the compositions can vary with different antibacterial agents, but generally can be 0.01 to 75% w/w, or 0.01 to 60% w/w, or 0.01 to 50% w/w, or any range or number therein (e.g., at least 0.01, 0.1, 0.5, 1, 2, 3, 4, 5, 10, 15, 20, 25, 30, 35, 40, 45, 50, 55, 60, 65, 70, and up to 75 wt. %).

C. Manufacture

The compositions of the invention may be manufactured by methods and equipment known in the art for manufacture of topical products and products designed for application to non-biological surfaces, such as medical devices. Such methods include, but are not limited to the use of mechanical mixers including LIGHTNIN propeller mixers; COWLES dissolvers; SILVERSON dispersers; counter-rotating side-scrapping mixers; homogenizers and dispersers, including in-line or in-tank rotor-stator homogenizers; and mills, including 3-roll mills, ointment mills, or rotor-stator mills. "All-in-one" vacuum mixing systems that have a rotating side-scrapping mixer plus an in-tank homogenizer may also be used. Such mixers include, but are not limited to OLSA mixers, FRYMA-KORUMA mixers, and LEE TM-MIX TURBO-SHEAR kettles. The compositions of the invention can be manufactured from small laboratory scale batches to full-scale production batches.

II. Bacterial Biofilms

The compositions of the invention are suitable for the reduction of bacteria in and/or elimination of both gram-positive and gram-negative bacterial biofilms. Non-limiting examples of gram-positive bacteria include *Staphylococcus* spp., such as *Staphylococcus aureus*, methicillin resistant *Staphylococcus aureus* (MRSA), and *Staphylococcus epidermidis; Streptococcus* spp, such as *Streptococcus pneumonia; Bacillus* spp.; *Listeria monocytogenes; enterococci* spp.; and lactic acid bacteria, such as *Lactobacillus plantarum* and *Lactococcus lactis*. Non-limiting examples of gram-negative bacteria include *Pseudomonas* spp., such as *Pseudomonas aeruginosa*; and *Escherichia coli*.

A. In-Vitro Biofilm Model

An in-vitro biofilm model was used to evaluate the biofilm efficacy of the formulations of the invention against bacterial biofilms. Bacteria are spotted onto a collagen matrix resting on a filter on a blood agar plate and incubated to allow biofilm formation. The model mimics in-vivo wound biofilms in that nutrients are provided from below the biofilm while topical treatments are applied at the air interface above. This in-vitro model and methodology is disclosed in the poster presentation, A Versatile In Vitro Biofilm Model Using Two Wound Pathogens to Screen Formulations, Van der Kar, et al., presented at the 2010 Wound Healing Society Annual Meeting, Poster BRC09, on Apr. 18, 2010 in Orlando, FL, and is herein incorporated by reference. Further in-vitro biofilm models and methodologies are disclosed in the following publications all of which are herein incorporated by reference: Penetration of Rifampin through *Staphylococcus epidermidis* Biofilms, Zheng, et al., Antimicrobial Agents and Chemotherapy, March 2002, p. 900-903; Oxygen Limitation Contributes to Antibiotic Tolerance of *Pseudomonas aeruginosa* in Biofilms, Borriello et al., Antimicrobial Agents and Chemotherapy, July 2004, p. 2659-2664; and Heterogeneity in *Pseudomonas aeruginosa* Biofilms Includes Expression of Ribosome Hibernation Factors in the Antibiotic-Tolerant Subpopulation and Hypoxia-Induced Stress Response in the Metabolically Active Population, Williamson et al., Journal of Bacteriology, February 2012, p. 2062-2073.

III. Methods of Use and Treatment

The compositions of the invention are useful for the reduction of bacteria in and/or elimination of bacterial biofilms on biological and non-biological surfaces, and are also useful for treatment of wounds, skin lesions, mucous membrane lesions, and other biological surfaces infected or contaminated with bacterial biofilms.

A. Biological Surfaces

The compositions of the invention are useful for reducing bacteria in and/or eliminating a bacterial biofilm on a biological surface by administering the compositions to the biological surface. Non-limiting examples of biological surfaces include wounds (including chronic and acute wounds), skin lesions, skin, mucous membranes, mucous membrane lesions, internal organs, body cavity, oral cavity, bone tissue, muscle tissue, nerve tissue, ocular tissue, urinary tract tissue, lung and trachea tissue, sinus tissue, ear tissue, dental tissue, gum tissue, nasal tissue, vascular tissue, cardiac tissue, epithelium, and epithelial lesions, and peritoneal tissue. Non-limiting examples of chronic wounds include diabetic foot ulcers, venous ulcers, arterial ulcers, decubitus ulcers, stasis ulcers, pressure ulcers, and burns. Non-limiting examples of acute wounds include cuts and surgical wounds. Non-limiting examples of skin lesions and mucous membrane lesions include blisters, ulcers, abrasions, warts, scrapes, and skin and mucosal infections such as staph or MRSA infections. Examples of skin lesions and mucous membrane lesions are disclosed in "Description of Skin Lesions", MacNeal, Robert J., the on-line Merck Manual Professional Version, March 2013. Skin lesions can appear on the epidermis, lips, ear canal, scalp, cuticle, nail bed, or genitalia. Mucous membrane lesions can appear on the oral mucosa, nasal mucosa, penile and vaginal mucosa, or anus.

B. Topical Treatment of Wounds

The compositions of the invention are useful for the treatment of wounds, including chronic wounds and acute wounds, infected or contaminated with bacterial biofilms, by topically administering the compositions to the wound. Non-limiting examples of chronic wounds include diabetic foot ulcers, venous ulcers, arterial ulcers, decubitus ulcers, stasis ulcers, pressure ulcers, and burns. Non-limiting examples of acute wounds include cuts and surgical wounds.

C. Topical Treatment of Skin Lesions and Mucous Membrane Lesions

The compositions of the invention are useful for the treatment of skin lesions or mucous membrane lesions infected or contaminated with bacterial biofilms by topically administering the compositions to the skin lesion or mucous membrane lesions. Non-limiting examples of skin lesions and mucous membrane lesions include blisters, ulcerations, abrasions, warts, scrapes, and skin and mucosal infections such as staph or MRSA infections. Skin lesions can appear on the epidermis, lips, ear canal, scalp, cuticle, nail bed, or genitalia. Mucous membrane lesions can appear on the oral mucosa, nasal mucosa, penile and vaginal mucosa, or anus.

D. Treatment of other Biological Surfaces

The compositions of the invention are useful for the treatment of other biological surfaces infected or contaminated with bacterial biofilms by administering the compositions to the biological surface. Non-limiting examples of other biological surfaces include internal organs, body cavity, oral cavity, bone tissue, muscle tissue, nerve tissue, ocular tissue, urinary tract tissue, lung and trachea tissue, sinus tissue, ear tissue, dental tissue, gum tissue, nasal tissue, vascular tissue, cardiac tissue, epithelium, and epithelial lesions, and peritoneal tissue.

E. Non-Biological Surfaces

The compositions of the invention are useful for reducing bacteria in and/or eliminating a bacterial biofilm on a non-biological surface, such as a medical device, by administering the compositions to the non-biological surface. Non-limiting examples of medical devices include urinary tract prostheses; urinary tract catheters, peritoneal membrane catheters, peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses; percutaneous sutures; and tracheal and ventilator tubing. The surface of an article of manufacturing, including medical devices, can be coated with the compositions of the inventions prior to the presence of a bacterial biofilm in order to prevent the formation of bacterial biofilms; or can be coated after the presence of a bacterial biofilm on the surface in order to reduce bacteria in and/or eliminate the bacterial biofilm on the surface.

IV. EXAMPLES

A. Example 1

Determination of Octanol-Water Partition Coefficient for CAPMUL MCM by ASTM Method 1. Prepared reference standard samples of compounds with known log P values shown in Table 2 at concentrations of approximately 200 mg/L in methanol.

2. Prepared test sample of CAPMUL MCM at a concentration of approximately 200 mg/mL in methanol.

3. Ran reference and test samples on HPLC using the parameters shown in Table 3.

4. Compared the retention times of the reference standards to the retention time of CAPMUL MCM to calculate the log P value of CAPMUL MCM as per ASTM method.

Figure 2:
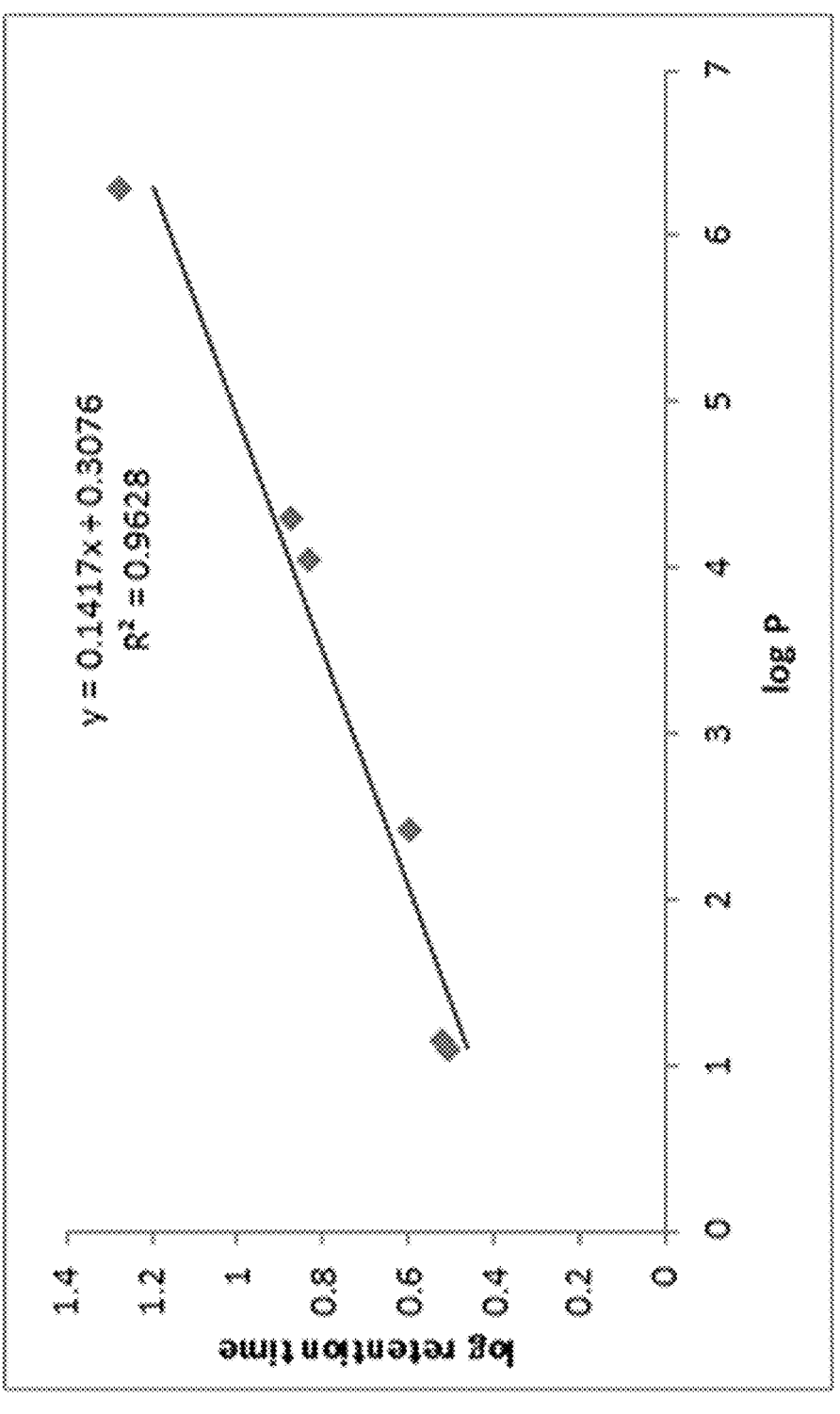
FIG. 2 shows the comparison of the retention times of the reference standards to the retention time of CAPMUL MCM to calculate the log P value of CAPMUL MCM as per ASTM method.

The retention times of the reference substances are shown in Table 2 and plotted in FIG. 2. The retention time of CAPMUL MCM is 3.011 giving a log P of 1.21 for CAPMUL MCM.

TABLE 2

| Reference Substance | log P | log retention time |
| --- | --- | --- |
| Anisyl alcohol | 1.1 | 0.5008 |
| Phenoxyethanol | 1.16 | 0.5161 |
| Diethyl phthalate | 2.42 | 0.5944 |
| Benzyl cinnamate | 4.06 | 0.8331 |
| Benzyl salicylate | 4.31 | 0.8719 |
| Dibutyl sebacate | 6.3 | 1.2709 |

TABLE 3

| Mobile Phase Solvent A | 40:60 ACN/H2O |
| Mobile Phase Solvent B | 70:30 ACN/H2O |
| Detector | 249 nm |
| Injection | 20 microliters |
| Flow Rate | 1 mL/min |
| Column | Luna C18(2) 5 micron, 100 angstroms, 250 × 4.6 mm |
| Gradient: | 0-15 min 100% A |
| | 15-15:50 Increase to 100% B |
| | 15:50-20 100% B |
| | 20-25 100% A |
| Temperature | 22° C. |

B. Example 2

Formulations

Various formulations were prepared and are shown in tables 4-9 below.

Cadexomer iodine based formulations are shown in Table 4.

TABLE 4

Cadexomer Iodine Based Formulations

| Component (% w/w) | Formula | | | | | | |
| --- | --- | --- | --- | --- | --- | --- | --- |
| | Cadexomer Iodine Control | Cadexomer Iodine/5% oil | Cadexomer Iodine/10% oil | Cadexomer Control | Cadexomer/ 10% oil control | Cadexomer Iodine/2.5% oil | Cadexomer Iodine 1% oil |
| PEG-400 | 38 | 34.3 | 30.4 | 41 | 30.4 | 36 | 37.2 |
| PEG-4000 | 10 | 9 | 8 | 10.7 | 8 | 9.5 | 9.8 |
| Poloxamer 184 | 2.1 | 1.8 | 1.6 | 2.2 | 1.6 | 1.9 | 1.9 |
| CAPMUL MCM NF | — | 5 | 10 | — | 10 | 2.5 | 1 |
| Cadexomer Iodine | 50 | 50 | 50 | — | — | 50 | 50 |
| Cadexomer Base | — | — | — | 46 | 50 | — | — |

Procedure (for concentration of each ingredient, see Table 4.): Mixed all ingredients except cadexomer iodine and/or cadexomer base at 70° C. until uniform. Added cadexomer iodine or cadexomer base and mixed until uniform. Cooled to room temperature (RT) while mixing.

Silver chloride based formulations are shown in Table 5.

TABLE 5

Silver Chloride Based Formulations

| Component (% w/w) | Formula | | |
| --- | --- | --- | --- |
| | Ag alone | Oil alone | Ag + Oil |
| HEC 250 HX (Aqualon) | 11 | 11 | 11 |
| Silver Chloride | 1 | — | 1 |
| CAPMUL MCM | — | 10 | 10 |
| Phenoxyethanol | 0.7 | 0.7 | 0.7 |
| PEG 600 | 39 | 35 | 34 |
| PEG 400 | 39 | 35 | 34 |
| PEG 3350 | 4 | 4 | 4 |
| ARISTOFLEX AVC | 1 | 1 | 1 |
| Glycerin | 4 | 4 | 4 |

Procedure (for concentration of each ingredient, see Table 5.): Homogenized PEG 600, PEG 400, PEG 3350, Glycerin, ARISTOFLEX AVC, CAPMUL MCM (if present), and Silver Chloride (if present) at high temperature using a Silverson homogenizer for 1 minute at 8000 rpm. Cooled the mixture to 50° C. and added HEC 250 HX while mixing. Continued mixing until the temperature was less than 35° C.

Other silver based formulations are shown in Table 6.

TABLE 6

Other Silver Based Formulations

| Component (% w/w) | Formula | | | | | | |
| --- | --- | --- | --- | --- | --- | --- | --- |
| | 1% AgNO3/ 9% oil | 1% AgCl/ 9% oil | 1% SSD/ 9% oil | 1% AgNO3 | 1% AgCl | 1% SSD | Placebo |
| Poloxamer 407 | 6 | 6 | 6 | 6 | 6 | 6 | 7 |
| Glycerin | 2 | 2 | 2 | 2 | 2 | 2 | 2 |
| Stearyl Alcohol | 3.8 | 3.8 | 3.8 | 3.8 | 3.7 | 3.7 | 3.0 |
| Polysorbate 60 | 3.7 | 3.7 | 3.7 | 3.8 | 3.7 | 3.7 | 3.2 |
| CAPMUL MCM NF | 9 | 9 | 9 | — | — | — | 9 |
| Isopropyl Myristate | 4.6 | 4.6 | 4.6 | 13.7 | 13.7 | 13.7 | 4.6 |
| Silver Nitrate | 1 | — | — | 1 | — | — | — |
| Silver Chloride | — | 1 | — | — | 1 | — | — |

TABLE 6-continued

| Other Silver Based Formulations | | | | | | |
| --- | --- | --- | --- | --- | --- | --- |
| | Formula | | | | | |
| Component (% w/w) | 1% AgNO3/ 9% oil | 1% AgCl/ 9% oil | 1% SSD/ 9% oil | 1% AgNO3 | 1% AgCl | 1% SSD | Placebo |
| Silver Sulfadiazine | — | — | 1 | — | — | 1 | — |
| PHOSPHOLIPON 90G | 2.3 | 2.3 | 2.3 | 2.3 | 2.3 | 2.3 | 2.3 |
| DI Water | qs ad 100 | qs ad 100 | qs ad 100 | qs ad 100 | qs ad 100 | qs ad 100 | qs ad 100 |

Procedure (for concentration of each ingredient, see Table 6.): Poloxamer 407, glycerin and water were mixed until dissolved at RT to form a water phase. Stearyl alcohol, polysorbate 60, isopropyl myristate, PHOSPHOLIPON G and CAPMUL MCM (if present) were mixed at 70° C. until clear to form an oil phase. The water phase and oil phase were combined and mixed at 70° C. for 2 hours and then cooled to RT while mixing. An active phase was made with water (10% w/w) and silver nitrate or silver chloride or silver sulfadiazine (SSD). The active phase (except for placebo) was then was added to the batch and mixed until uniform.

Povidone-iodine based formulations are shown in Table 7.

TABLE 7

| Povidone-Iodine Based Formulations | | |
| --- | --- | --- |
| | Formula | |
| Component (% w/w) | Placebo plus oil | 5% PVI | 5% PVI + 10% oil |
| Poloxamer-407 | 15.0 | 15.1 | 14.6 |
| Propylene Glycol | 5.0 | 5.0 | 5.4 |
| Povidone-Iodine | — | 5.0 | 4.9 |
| CAPMUL MCM NF | 10.0 | — | 10.1 |
| DI Water | qs ad 100 | qs ad 100 | qs ad 100 |

Procedure (for concentration of each ingredient, see Table 7.): Poloxamer-407 and propylene glycol were dissolved in water. Povidone Iodine and/or CAPMUL MCM were added while mixing and mixed until homogenous. The formulations containing povidone-iodine were brown solutions Gentamicin based formulations are shown in Table 8.

TABLE 8

| Gentamicin Based Formulations | | |
| --- | --- | --- |
| | Formula | |
| Component (% w/w) | Placebo plus oil | 0.7% GENTA | 0.7% GENTA + 10% oil |
| Poloxamer-407 | 15.0 | 14.8 | 15.0 |
| Propylene Glycol | 5.0 | 5.0 | 5.0 |
| Gentamicin Sulfate | — | 0.7 | 0.7 |
| CAPMUL MCM NF | 10.0 | — | 10.8 |
| DI Water | qs ad 100 | qs ad 100 | qs ad 100 |

Procedure (for concentration of each ingredient, see Table 8.): Poloxamer-407 and propylene glycol were dissolved in water. Gentamicin sulfate and/or CAPMUL MCM were added while mixing and mixed until homogenous. The formulations containing CAPMUL MCM were thick, ringing gels. The viscosity of the ringing gel formulation "0.7% GENTA+10% oil" was 89,000 cps as measured using a Brookfield RV viscometer with a small sample adapter, spindle #14, at room temperature (22°-25° C.), at 10 rpm for 1 minute.

Colistin based formulations are shown in Table 9.

TABLE 9

| Colistin Based Formulations | | |
| --- | --- | --- |
| | Formula | |
| Component (% w/w) | Placebo plus oil | 0.1% Colistin Sulfate | 0.1% Colistin Sulfate + 10% oil |
| Poloxamer-407 | 15.0 | 15.0 | 15.0 |
| Propylene Glycol | 5.0 | 5.0 | 5.1 |
| Colistin Sulfate | — | 0.1 | 0.1 |
| CAPMUL MCM NF | 10.0 | — | 10.0 |
| DI Water | qs ad 100 | qs ad 100 | qs ad 100 |

Procedure (for concentration of each ingredient, see Table 9.): Poloxamer-407 and propylene glycol were dissolved in water. Colistin sulfate and/or CAPMUL MCM were added while mixing and mixed until homogenous. The formulations containing CAPMUL MCM were thick, ringing gels.

C. Example 3

In-vitro *P. aeruginosa* Biofilm Model with Various Treatment Formulations

*P. aeruginosa* ATCC 27312 was grown overnight on tryptic soy agar (TSA) at 37° C. The next day, a single colony was picked and passed into tryptic soy broth (TSB), then grown at 37° C. overnight with shaking (150 rpm). The overnight culture was diluted to ~1.5×10^8 cfu/mL in PBS (inoculum). Tryptic soy agar with 5% sheep blood (TSAB) plates were prepared with six 13 mm black 0.2 micron TEFLON filters. Each 13 mm filter had a single 4 mm collagen plug placed in the center and was then inoculated with 3 μL of inoculum placed on the center of the plug (13 mm filter plus inoculated plug=colony biofilm assembly or CBFA). The CBFA plates were transferred to a 37° C. incubator and incubated for 24 hours. At the end of the incubation, growth was sampled and treatment with the test formulations of Example 2 was started. The test formulations for the cadexomer iodine based formulations (Table 4) were mixed 50/50 (weight/volume) with PBS and applied (200 μL) to PBS moistened (200 μL) 13 mm TELFA non-adherent dressing squares. The other test formulations (gel and liquid formulations from Tables 5-9) were applied directly to the PBS moistened TEFLA squares (the liquid formulations were mixed for 10 seconds prior to the application). The treatments were applied with the formulation directly in contact with the biofilm (TELFA on top) and gently tamped down to ensure contact with the biofilm (moist control was TELFA only). The treated CBFA plates were transferred to the 37° C. incubator and incubated for 24 hours. At the end of the incubation, the treated CBFA were recovered into 5 mL DE Broth PBS and vortexed at 2500 rpm for 2 minutes to knock off the treatments and resuspend any surviving bacteria. The recoveries were serially diluted (1:10 eight point dilution series in PBS broth) and 10 μL volumes spotted on Charcoal Agar plates (the plates serve to neutralize any active treatments). The plates were allowed to dry and incubated at 37° C. overnight with colony counts determined the next day. Counts were converted to colony forming units per milliliter and transformed to log values. Efficacy was determined by subtracting the log cfu/mL value of a treatment from the moist control to generate a log reduction value in addition to direct comparison of recovered log cfu/mL.

Figure 3:
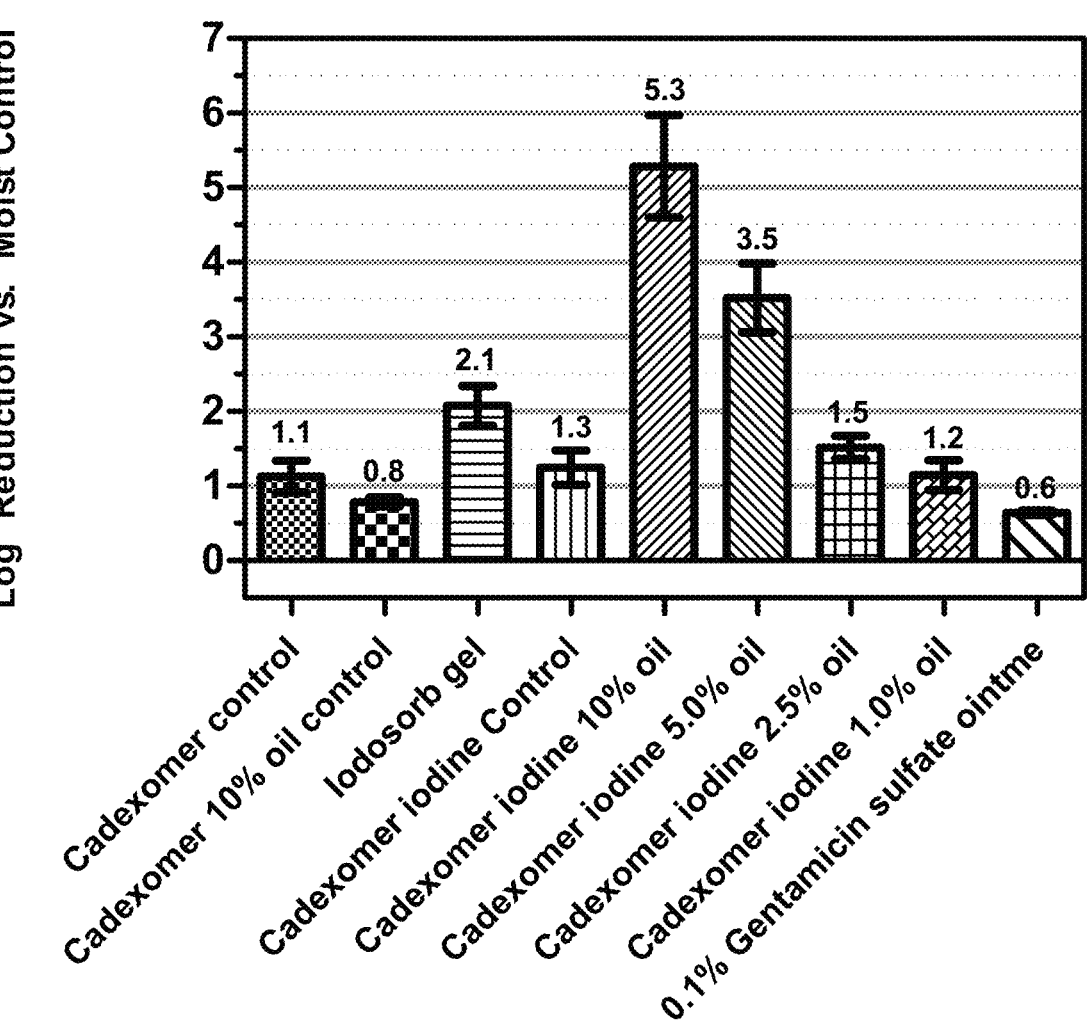
FIG. 3 shows the log reduction of bacteria in the *P. aeruginosa* biofilm model after treatment with the treatment formulations from Example 2 (cadexomer iodine based formulations) vs. moist control.
Figure 4:
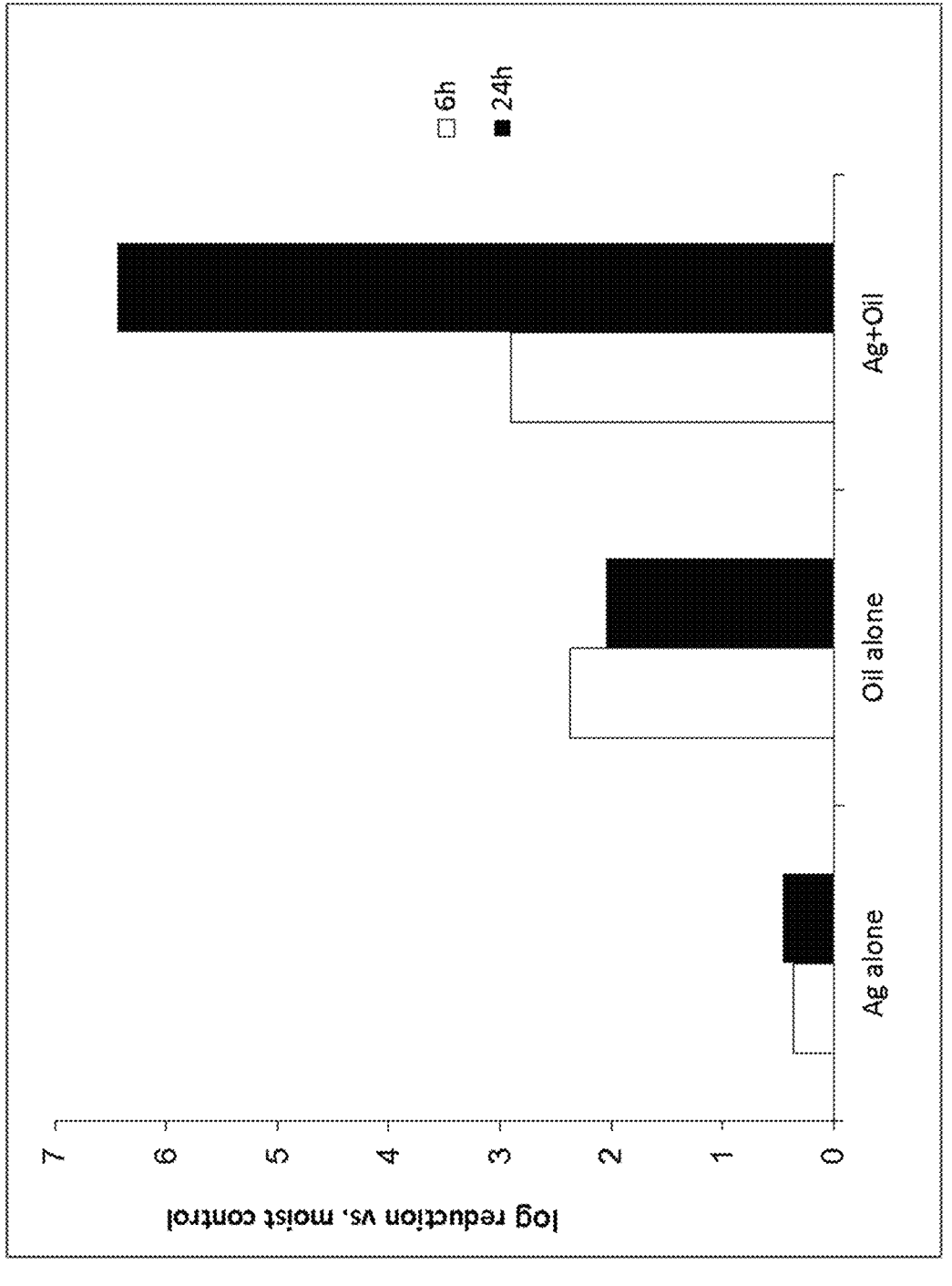
FIG. 4 shows the log reduction of bacteria in the *P. aeruginosa* biofilm model after treatment with the treatment formulations from Example 2 (silver chloride based formulations) vs. moist control.
Figure 5:
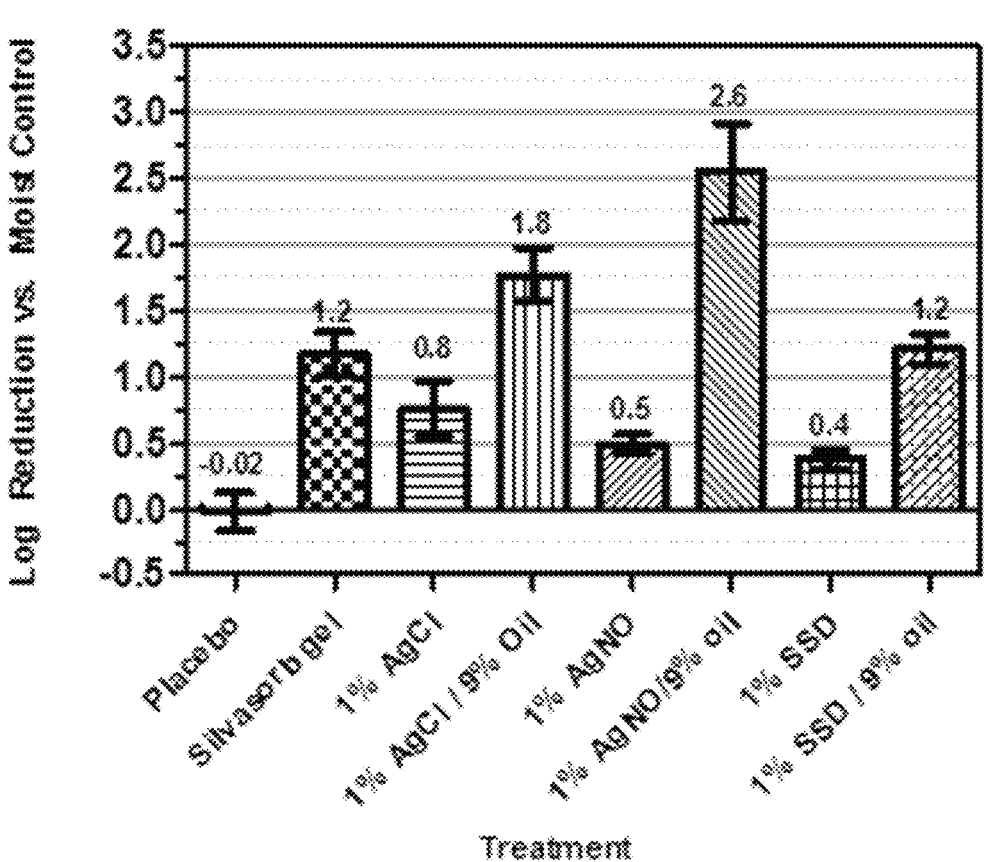
FIG. 5 shows the log reduction of bacteria in the *P. aeruginosa* biofilm model after treatment with the treatment formulations from Example 2 (other silver based formulations) vs. moist control.
Figure 6:
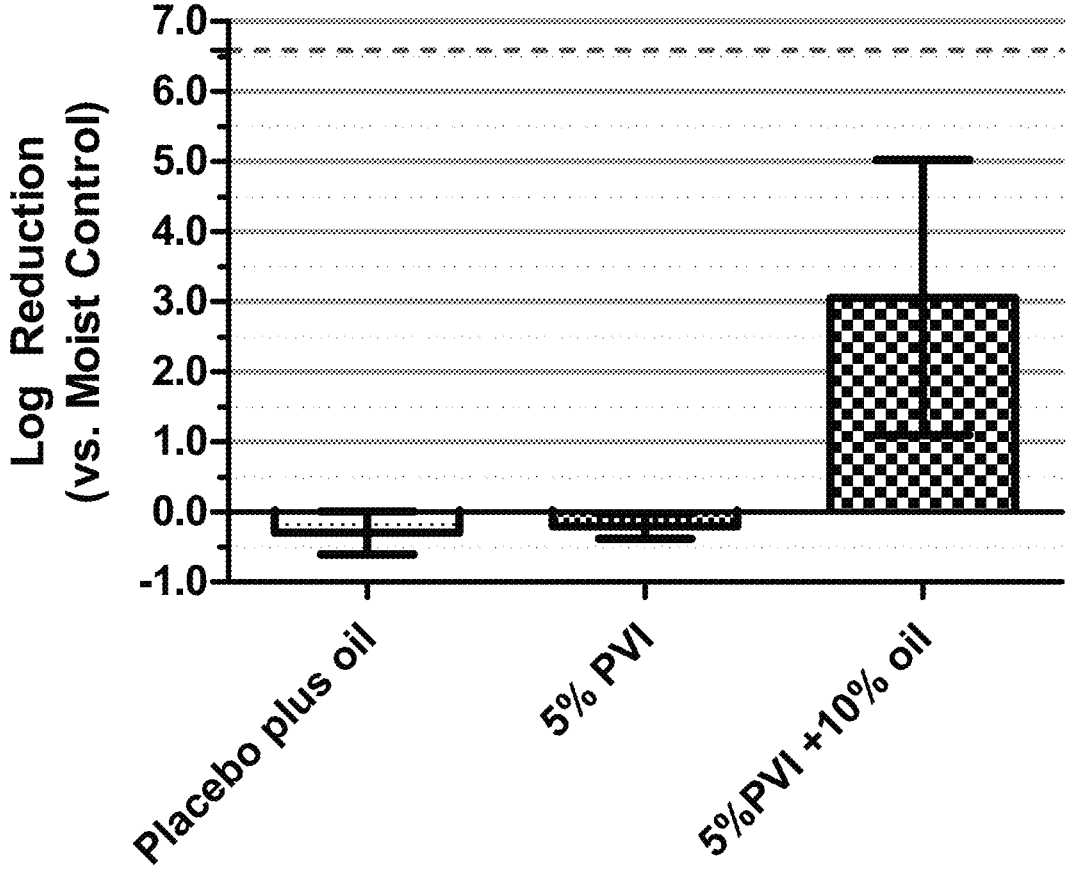
FIG. 6 shows the log reduction of bacteria in the *P. aeruginosa* biofilm model after treatment with the treatment formulations from Example 2 (povidone-iodine based formulations) vs. moist control.
Figure 7:
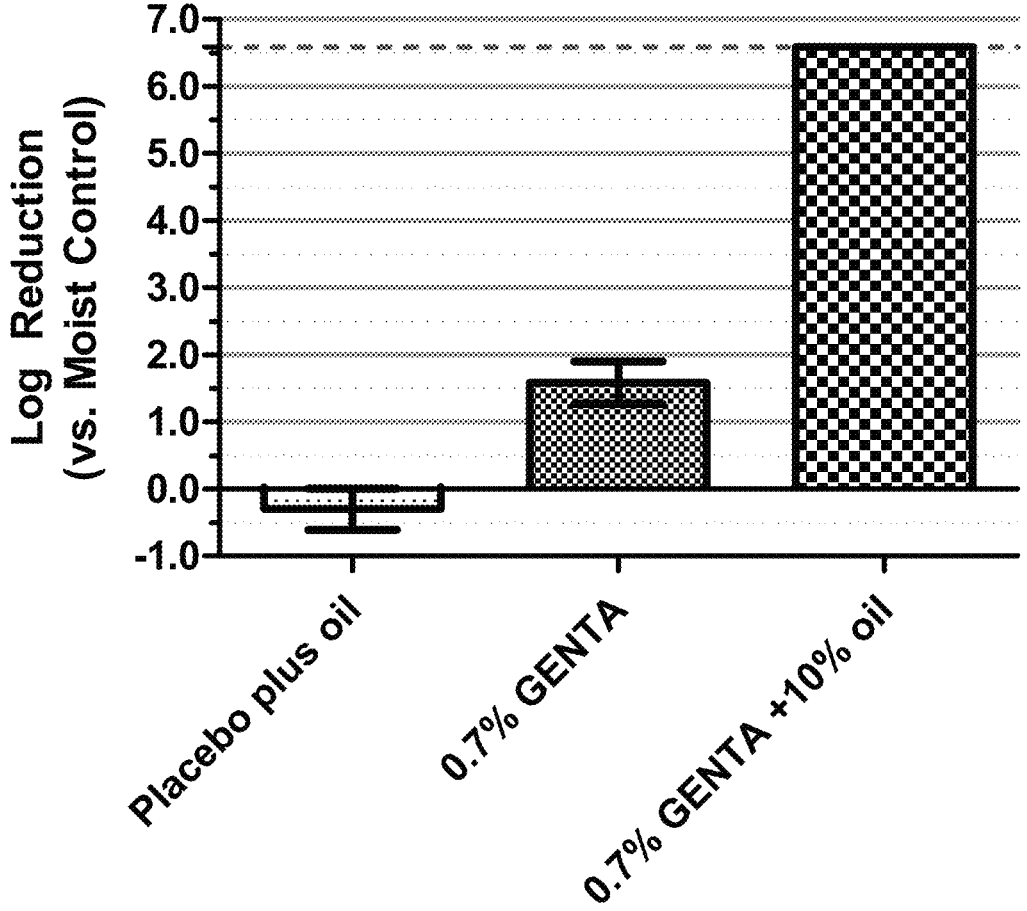
FIG. 7 shows the log reduction of bacteria in the *P. aeruginosa* biofilm model after treatment with the treatment formulations from Example 2 (gentamicin based formulations) vs. moist control.
Figure 8:
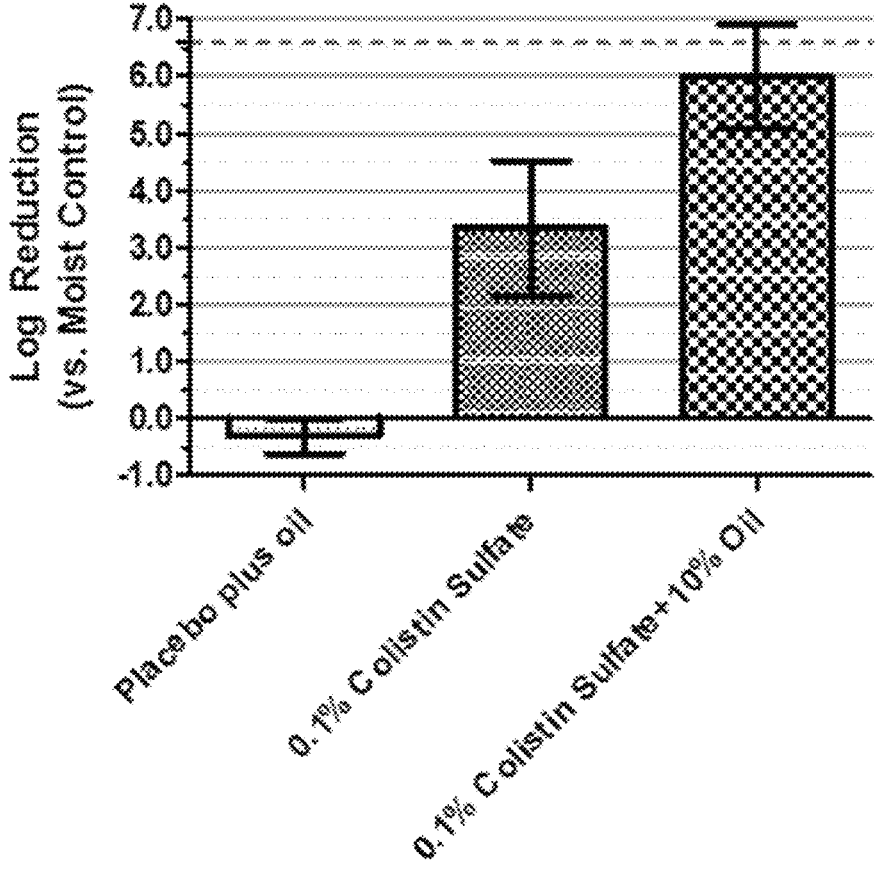
FIG. 8 shows the log reduction of bacteria in the *P. aeruginosa* biofilm model after treatment with the treatment formulations from Example 2 (colistin based formulations) vs. moist control.

The results of the log reduction of bacteria in the biofilm model after treatment with the treatment formulations from Example 2 (cadexomer iodine based formulations—Table 4) vs. moist control are shown in FIG. 3. The results of the log reduction of bacteria in the biofilm model after treatment with the treatment formulations from Example 2 (silver chloride based formulations—Table 5) vs. moist control are shown in FIG. 4. Results of the log reduction of bacteria in the biofilm model after treatment with the treatment formulations from Example 2 (other silver based formulations—Table 6) vs. moist control are shown in FIG. 5. The results of the log reduction of bacteria in the biofilm model after treatment with the treatment formulations from Example 2 (povidone-iodine based formulations—Table 7) vs. moist control are shown in FIG. 6. The results of the log reduction of bacteria in the biofilm model after treatment with the treatment formulations from Example 2 (gentamicin based formulations—Table 8) vs. moist control are shown in FIG. 7. The results of the log reduction of bacteria in the biofilm model after treatment with the treatment formulations from Example 2 (colistin based formulation—Table 9) vs. moist control are shown in FIG. 8.

The results in FIG. 5 show the cumulative log reduction effect of the "1% AgCl" formulation plus the "Placebo" formulation was less than the log reduction effect of the "1% AgCl/9% oil" formulation; the cumulative log reduction effect of the "1% AgNO" formulation plus the "Placebo" formulation was less than the log reduction effect of the "1% AgNO/9% oil" formulation; and the cumulative log reduction effect of the "1% SSD" formulation plus the "Placebo" formulation was less than the log reduction effect of the "1% SSD/9% oil" formulation. These results indicate synergistic antibacterial activity by the combination of the antibacterial agent and the medium polarity oil.

The results in FIG. 4 show the cumulative log reduction effect of the "Ag alone" formulation plus the "Oil alone" formulation is less than the log reduction effect of the "Ag+Oil" formulation at 24 hours indicating synergistic antibacterial activity by the combination of the antibacterial agent and the medium polarity oil.

The results in FIG. 3 show the cumulative log reduction effect of the "Cadexomer 10% oil control" formulation plus the "Cadexomer Iodine Control" formulation is less than the log reduction effect of the "Cadexomer Iodine 10% oil" formulation indicating synergistic antibacterial activity by the combination of the antibacterial agent and the medium polarity oil.

The results in FIG. 6 show the cumulative log reduction effect of the "Placebo plus oil" formulation plus the "5% PVI" formulation is less than the log reduction effect of the "5% PVI+10% oil" formulation indicating synergistic antibacterial activity by the combination of the antibacterial agent and the medium polarity oil.

The results in FIG. 7 show the cumulative log reduction effect of the "Placebo plus oil" formulation plus the "0.7% GENTA" formulation is less than the log reduction effect of the "0.7% GENTA+10% oil" formulation indicating synergistic antibacterial activity by the combination of the antibacterial agent and the medium polarity oil.

The results in FIG. 8 show the cumulative log reduction effect of the "Placebo plus oil" formulation plus the "0.1% colistin sulfate" formulation is less than the log reduction effect of the "0.1% colistin sulfate+10% oil" formulation indicating synergistic antibacterial activity by the combination of the antibacterial agent and the medium polarity oil.

The invention claimed is:

1. A method of treating a wound, mucous membrane lesion, or skin lesion; wherein the wound, mucous membrane lesion and skin lesion is infected or contaminated with a bacterial biofilm, the method comprising topically administering to the wound, mucous membrane lesion, or skin lesion a composition comprising a combination of a pharmaceutical carrier and an antibacterial agent, wherein the pharmaceutical carrier is not an emulsion, wherein the composition does not include a silver compound, an organic acid, and a chelating agent, wherein the antibacterial agent comprises at least one medium polarity oil having an octanol-water partition coefficient (log P) of 0.5 to 2.0 and at least one iodine compound, wherein the at least one medium polarity oil is benzyl alcohol or propyl gallate and is present at a concentration of 8% w/w to 12% w/w, wherein the at least one iodine compound is:

povidone-iodine present at a concentration of about 5% w/w; or cadexomer-iodine is present at a concentration of 45% w/w to 55% w/w, and wherein the combination of the at least one medium polarity oil and the at least one iodine compound exhibits synergistic antibacterial activity against the biofilm.

2. The method of claim 1, wherein the pharmaceutical carrier is suitable for topical treatment and is a solution, suspension, liquid, gel, ringing gel, ointment, paste, aerosol spray, aerosol foam, non-aerosol spray, non-aerosol foam, film, or sheet.

3. The method of claim 1, wherein the at least one medium polarity oil is present at a concentration of 9% w/w to 11% w/w.

4. The method of claim 1, wherein the bacterial biofilm is a gram-positive or a gram-negative bacterial biofilm.

5. The method of claim 4, wherein the gram-positive bacterial biofilm is a *Staphylococcus* sp, and wherein the gram-negative bacterial biofilm is a *Pseudomonas* sp.

6. The method of claim 1, wherein:

the wound is a chronic wound, and the chronic wound is a diabetic foot ulcer, venous ulcer, arterial ulcer, decubitus ulcer, stasis ulcer, pressure ulcer, or burn; or the skin lesion or mucous membrane lesion is a blister, ulceration, abrasion, wart, scrape, or infection.

7. A method of reducing bacteria in or eliminating a bacterial biofilm on a biological surface, the method comprising administering to the biological surface a composition comprising a combination of a pharmaceutical carrier and an antibacterial agent, wherein the pharmaceutical carrier is not an emulsion, wherein the composition does not include a silver compound, an organic acid, and a chelating agent, wherein the antibacterial agent comprises at least one medium polarity oil having an octanol-water partition coefficient (log P) of 0.5 to 2.0 and at least one iodine compound, wherein the at least one medium polarity oil is benzyl alcohol or propyl gallate and is present at a concentration of 8% w/w to 12% w/w, wherein the at least one iodine compound is:

povidone-iodine and is present at a concentration of about 5% w/w; or cadexomer-iodine is present at a concentration of 45% w/w to 55% w/w, and wherein the combination of the at least one medium polarity oil and the at least one iodine compound exhibits synergistic antibacterial activity against the biofilm.

8. The method of claim 7, wherein the pharmaceutical carrier is suitable for application to a biological surface and is a lotion, solution, suspension, liquid, emulsion, cream, gel, ringing gel, ointment, paste, aerosol spray, aerosol foam, non-aerosol spray, non-aerosol foam, film, or sheet.

9. The method of claim 7, wherein the bacterial biofilm is a *Staphylococcus* sp. biofilm or a *Pseudomonas* sp. biofilm.

10. The method of claim 7, wherein the biological surface is:

a chronic wound, and the chronic wound is a diabetic foot ulcer, venous ulcer, arterial ulcer, decubitus ulcer, stasis ulcer, pressure ulcer, or burn; or a skin lesion or mucous membrane lesion, and the skin lesion or mucous membrane lesion is a blister, ulceration, abrasion, wart, scrape, or infection.

11. The method of claim 7, wherein the at least one medium polarity oil is present at a concentration of 9% w/w to 11% w/w.

\* \* \* \* \*